United States Patent
Zurn

(10) Patent No.: US 9,833,207 B2
(45) Date of Patent: Dec. 5, 2017

(54) ANALYSIS AND CLEARING MODULE, SYSTEM AND METHOD

(76) Inventor: William Harrison Zurn, Sunnyvale, CA (US)

(*) Notice: Subject to any disclaimer, the term of this patent is extended or adjusted under 35 U.S.C. 154(b) by 1062 days.

(21) Appl. No.: 13/569,204

(22) Filed: Aug. 8, 2012

(65) Prior Publication Data

US 2014/0046146 A1   Feb. 13, 2014

(51) Int. Cl.
| | | |
|---|---|---|
| A61B 5/00 | (2006.01) | |
| A61B 6/00 | (2006.01) | |
| A61N 5/06 | (2006.01) | |
| A61B 18/20 | (2006.01) | |
| A61B 18/24 | (2006.01) | |
| A61B 5/07 | (2006.01) | |
| A61B 5/08 | (2006.01) | |
| A61B 5/145 | (2006.01) | |
| A61B 18/00 | (2006.01) | |
| A61B 5/055 | (2006.01) | |
| A61B 5/06 | (2006.01) | |
| A61B 6/03 | (2006.01) | |
| A61B 8/08 | (2006.01) | |

(Continued)

(52) U.S. Cl.
CPC .......... *A61B 6/4417* (2013.01); *A61B 5/0031* (2013.01); *A61B 5/0035* (2013.01); *A61B 5/076* (2013.01); *A61B 5/08* (2013.01); *A61B 5/14503* (2013.01); *A61B 5/14507* (2013.01); *A61B 6/504* (2013.01); *A61B 18/20* (2013.01); *A61B 18/245* (2013.01); *A61N 5/0603* (2013.01); *A61B 5/055* (2013.01); *A61B 5/062* (2013.01); *A61B 6/03* (2013.01); *A61B 6/5247* (2013.01); *A61B 8/0891* (2013.01); *A61B 2018/00505* (2013.01); *A61B 2018/00541* (2013.01); *A61B 2034/2065* (2016.02); *A61B 2090/374* (2016.02); *A61B 2560/0219* (2013.01); *A61N 2005/0604* (2013.01)

(58) Field of Classification Search
None
See application file for complete search history.

(56) References Cited

U.S. PATENT DOCUMENTS 3,657,744 A    4/1972   Ersek
4,061,134 A   12/1977   Samuels et al.
(Continued)

OTHER PUBLICATIONS

Sawant., Enhancing Personal Health Monitoring Systems with FPGA Technology, pp. 4-6, 2012.

(Continued)

*Primary Examiner* — Tse Chen
*Assistant Examiner* — Joanne Hoffman
(74) *Attorney, Agent, or Firm* — Law Office of Alan W. Cannon

(57) ABSTRACT

Modules, systems and methods for clearing substances from a living body are disclosed. A module may include an instructions receiver configured to receive wireless transmissions of instructions from a master controller located outside of the body when the module is inside the body; an energy receiver configured to receive wireless transmission of non-destructive energy from the master controller located outside of the body when the module is inside the body; an energy converter configured to convert the non-destructive energy received to destructive energy; and an energy emitter configured to emit the destructive energy.

7 Claims, 10 Drawing Sheets

(51) Int. Cl.
*A61B 90/00* (2016.01)
*A61B 34/20* (2016.01)

(56) References Cited

U.S. PATENT DOCUMENTS

| | | | |
|---|---|---|---|
| 4,140,126 A | 2/1979 | Choudhury | |
| 4,210,666 A | 7/1980 | Munson, Jr. | |
| 4,276,874 A | 7/1981 | Wolvek et al. | |
| 4,557,626 A | 12/1985 | McKay et al. | |
| 4,560,374 A | 12/1985 | Hammerslag | |
| 4,617,932 A | 10/1986 | Kornberg | |
| 4,650,466 A | 3/1987 | Luther | |
| 4,654,024 A | 3/1987 | Crittenden et al. | |
| 4,655,771 A | 4/1987 | Wallsten | |
| 4,672,961 A | 6/1987 | Davies | |
| 4,728,328 A | 3/1988 | Hughes et al. | |
| 4,732,152 A | 3/1988 | Wallsten et al. | |
| 4,739,762 A | 4/1988 | Palmaz | |
| 4,787,899 A | 11/1988 | Lazarus | |
| 4,795,458 A | 1/1989 | Regan | |
| 4,799,925 A | 1/1989 | Rosenblatt | |
| 4,819,632 A | 4/1989 | Davies | |
| 4,830,003 A | 5/1989 | Wolff et al. | |
| 4,892,539 A | 1/1990 | Koch | |
| 4,913,141 A | 4/1990 | Hillstead | |
| 4,954,126 A | 9/1990 | Wallsten | |
| 4,969,896 A | 11/1990 | Shors | |
| 4,994,071 A | 2/1991 | MacGregor | |
| 4,995,386 A | 2/1991 | Ng | |
| 4,998,539 A | 3/1991 | Delsanti et al. | |
| 4,998,972 A | 3/1991 | Chin et al. | |
| 5,024,671 A | 6/1991 | Tu | |
| 5,026,377 A | 6/1991 | Burton et al. | |
| 5,035,706 A | 7/1991 | Giantureo et al. | |
| 5,047,050 A | 9/1991 | Arpesani | |
| 5,078,726 A | 1/1992 | Kreamer | |
| 5,084,065 A | 1/1992 | Weldon | |
| 5,090,959 A | 2/1992 | Samson et al. | |
| 5,100,426 A | 3/1992 | Nixon | |
| 5,102,417 A | 4/1992 | Palmaz | |
| 5,104,399 A | 4/1992 | Lazarus | |
| 5,104,404 A | 4/1992 | Wolff | |
| 5,122,154 A | 6/1992 | Rhodes | |
| 5,123,917 A | 6/1992 | Lee | |
| 5,158,548 A | 10/1992 | Lau | |
| 5,192,297 A | 3/1993 | Hull | |
| 5,201,757 A | 4/1993 | Heyn et al. | |
| 5,207,695 A | 5/1993 | Trout, III | |
| 5,219,355 A | 6/1993 | Parodi et al. | |
| 5,275,622 A | 1/1994 | Lazarus et al. | |
| 5,282,824 A | 2/1994 | Gianturco | |
| 5,316,023 A | 5/1994 | Palmaz et al. | |
| 5,333,969 A | 8/1994 | Blaha et al. | |
| 5,360,443 A | 11/1994 | Barone et al. | |
| 5,362,176 A | 11/1994 | Sovik et al. | |
| 5,395,334 A | 3/1995 | Keith et al. | |
| 5,397,345 A | 3/1995 | Lazarus | |
| 5,489,295 A | 2/1996 | Piplani et al. | |
| 5,549,412 A | 8/1996 | Malone et al. | |
| 5,562,728 A | 10/1996 | Lazarus | |
| 5,609,625 A | 3/1997 | Piplani | |
| 5,628,783 A | 5/1997 | Quiachon | |
| 5,662,700 A | 9/1997 | Lazarus | |
| 5,669,936 A | 9/1997 | Lazarus | |
| 5,721,685 A | 2/1998 | Holland et al. | |
| 5,725,842 A | 3/1998 | Boucher, Jr. et al. | |
| 5,741,246 A | 4/1998 | Prescott | |
| 5,824,015 A | 10/1998 | Sawyer | |
| 5,830,209 A | 11/1998 | Savage et al. | |
| 5,855,599 A | 1/1999 | Wan | |
| 5,902,567 A | 5/1999 | Boucher, Jr. | |
| 5,932,481 A | 8/1999 | Pon et al. | |
| 5,951,566 A | 9/1999 | Lev | |
| 5,964,223 A | 10/1999 | Baran | |
| 6,004,269 A | 12/1999 | Crowley et al. | |
| 6,019,784 A | 2/2000 | Hines | |
| 6,022,527 A | 2/2000 | Boucher, Jr. et al. | |
| 6,027,863 A | 2/2000 | Donadio, III | |
| 6,033,398 A | 3/2000 | Farley et al. | |
| 6,074,374 A | 6/2000 | Fulton | |
| 6,107,004 A | 8/2000 | Donadio, III | |
| 6,133,247 A | 10/2000 | Boucher, Jr. | |
| 6,139,511 A | 10/2000 | Huter et al. | |
| 6,146,814 A | 11/2000 | Millet | |
| 6,168,579 B1 | 1/2001 | Tsugita | |
| 6,203,732 B1 | 3/2001 | Clubb et al. | |
| 6,210,362 B1 | 4/2001 | Ponzi | |
| 6,214,536 B1 | 4/2001 | Boucher, Jr. | |
| 6,240,312 B1* | 5/2001 | Alfano | A61B 1/00016 128/903 |
| 6,241,745 B1 | 6/2001 | Rosenthal | |
| 6,251,128 B1 | 6/2001 | Knopp et al. | |
| 6,374,476 B1 | 4/2002 | Ponzi et al. | |
| 6,398,792 B1 | 6/2002 | O'Connor | |
| 6,520,934 B1 | 2/2003 | Lee et al. | |
| 6,524,303 B1 | 2/2003 | Garibaldi | |
| 6,595,949 B1 | 7/2003 | Shapiro | |
| 6,620,148 B1 | 9/2003 | Tsugita | |
| 6,673,104 B2 | 1/2004 | Barry | |
| 6,696,335 B2 | 2/2004 | Bonart | |
| 6,786,896 B1 | 9/2004 | Madhani et al. | |
| 6,926,670 B2 | 8/2005 | Rich et al. | |
| 6,968,743 B2 | 11/2005 | Rich et al. | |
| 6,980,843 B2 | 12/2005 | Eng et al. | |
| 6,986,757 B1 | 1/2006 | Kumasaki et al. | |
| 6,997,918 B2 | 2/2006 | Soltesz et al. | |
| 6,998,358 B2 | 2/2006 | French et al. | |
| 7,137,393 B2 | 11/2006 | Pivovarov | |
| 7,204,252 B2 | 4/2007 | Johnson | |
| 7,242,301 B2 | 7/2007 | August et al. | |
| 7,278,429 B2 | 10/2007 | Johnson | |
| 7,607,440 B2 | 10/2009 | Coste-Maniere et al. | |
| 7,647,831 B2 | 1/2010 | Corcoran et al. | |
| 7,654,130 B2 | 2/2010 | Shah et al. | |
| 7,699,059 B2 | 4/2010 | Fonseca et al. | |
| 7,790,226 B2 | 9/2010 | Tai et al. | |
| 7,839,153 B2 | 11/2010 | Joy et al. | |
| 7,851,456 B2 | 12/2010 | Boyer et al. | |
| 7,899,578 B2 | 3/2011 | Prisco et al. | |
| 7,907,166 B2 | 3/2011 | Lamprecht et al. | |
| 7,914,442 B1* | 3/2011 | Gazdzinski | A61B 1/00009 600/109 |
| 7,929,741 B2 | 4/2011 | Guiliguian et al. | |
| 7,938,123 B2 | 5/2011 | Danek et al. | |
| 7,967,754 B2 | 6/2011 | Knight | |
| 7,976,779 B2* | 7/2011 | Tai | G01N 30/34 204/450 |
| 7,979,108 B2 | 7/2011 | Zurn | |
| 2002/0133219 A1 | 9/2002 | Barry | |
| 2005/0159802 A1 | 7/2005 | Furst et al. | |
| 2006/0224154 A1 | 10/2006 | Shadduck et al. | |
| 2006/0232417 A1 | 10/2006 | August et al. | |
| 2007/0010702 A1 | 1/2007 | Wang et al. | |
| 2007/0135887 A1 | 6/2007 | Maschke | |
| 2007/0167702 A1 | 7/2007 | Hasser et al. | |
| 2007/0210786 A1 | 9/2007 | Allen et al. | |
| 2008/0004595 A1 | 1/2008 | Viswanathan et al. | |
| 2008/0021307 A1 | 1/2008 | Freeman et al. | |
| 2009/0005859 A1 | 1/2009 | Keilman | |
| 2009/0062639 A1 | 3/2009 | Zurn | |
| 2009/0318762 A1* | 12/2009 | Segawa | A61B 1/00158 600/118 |
| 2011/0166416 A1* | 7/2011 | Katayama | A61B 1/00082 600/104 |
| 2012/0147329 A1* | 6/2012 | Papac | A61B 19/5202 351/213 |

OTHER PUBLICATIONS

Seward., Fantastic voyage through the cardiovascular system. 2003, 5, pp. 8-11.
Shimizu et al., Easier to Swallow, pp. 14-15, 2012.

(56) References Cited

OTHER PUBLICATIONS

Taranovich., Medical Sensors Encompass Biomedical Electronics, 6. pgs, 2011.
Timothy F. Kirn, European Series: Carotid Stent vs. Endarterectomy, VascularWeb,Provided by the Society for Vascular Surgery ,vol. 2—2006 Issue 3.
Timothy F. Kirn, Endovascular Emergency Repair of Ruptured AAA Uses Balloon Technique, Vascular Web,Provided by the Society for Vascular Surgery ,vol. 2—2006 Issue 3.
Timothy F. Kirn, Endovascular AAA Repair Is Gaining, Expert Asserts, VascularWeb, Provided by the Society for Vascular Surgery ,vol. 1—2005 Issue 2.
Timothy F. Kirn, Endovascular Aortic Repair Less Harmful to Heart?, VascularWeb,Provided by the Society for Vascular Surgery ,vol. 2—2006 Issue 3.
Timothy J. Parker, Pixellated NaI(T1). For Enhanced Performance 2001, 2 pgs.
Tupta et al., Tools and techniques for testing Nanotech, pp. 85-89, 2011.
Veith, The Rush to Stent: A Cause for Concern, VascularWeb, Provided by the Society for Vascular Surgery, vol. 2—2006 Issue 2.
Weiler., High-power pico- and femtosecond lasers enable new applications. Oct. 2011, pp. 55-61.
Wireless, Self-Propelled Medical Implant on the Horizon, 2 pgs, 2012.
Woo., MD, Acute Aortic Dissection: A Case for Specialized Centers Colleague Commentary, VascularWeb, Provided by the Society for Vascular Surgery, vol. 2—2006 Issue 3.
Zimmermann et al., Robot-assisted Navigated Neuroendoscopy, Neurosurgery: vol. 51(6) Dec. 2002 pp. 1446-1452.
Allan., Microelectronics: The Medical Industry's Mini Marvels, 5 pgs. 2011.
Allan., System-Level Applications make MEMS Ubiquitous, pp. 61-64, 2012.
Bridges., FDA: Stent Patients Face Blood Clot Risk, Associated Press, pp. 1-3, 2006.
Bridges, FDA: Heart Stents Don't Up Risk of Death, Associated Press, 2 pgs., 2006.
Breit, Unlocking the Potential of RF MEMS with New Design Appraches, pp. 10-11, 2012.
Broockman, FCC'S Secret Spectrum, pp. 84-85, 2012.
Bonanomi, et al., Microelectromechanical systems for endoscopic cardiac surgery. 2003, vol. 126, No. 3, pp. 851-852.
Busch, Detecting Ions in Mass Spectrometers with the Faraday Cup, 6 pgs., 2011.
Buntz, Theoretical Physicist Michio Kaku Predicts the Future of Healthcare, 3 pgs., 2012.
CAT Scan (CT)—Body, download Mar. 19, 2009, pp. 1-6. http://www.radiologyinfo.org/en/info.cfm?PG=bodyct.
Carey, No One Wanted to Hear, Business Week, Oct. 9, 2006, pp. 91-92.
Canavan, Nanotechnology, the future, and the FDA Articles Drug Discovery and Development, 4 pgs, 2011.
Chatterjee., Contributing Technical Editor. New devices for nanoelectronics., Mar. 3, 2011, pp. 18.
Chatterjee., Driving toward milivolt electronics, pp. 22, 2011.
Comerford., Special namotubes may up Li battery's energy density—Electronic Products, 2011, pp. 2 pgs.
Cordes, et al., CMOS cameras allow robut active stabilization of laser beams. Aug. 2011, 3 pages.
Colin., SLI eliminates the need for touch in MEMS applications, pp. 16, 2012.
Criado et al, Talent LPS AAA stent graft: Results of a pivotal clinical trial, Journal of Vascular Surgery vol. 37, No. 4 , 2006, pp. 1-10.

Chai., Atomic and Molecular Manipulation to Drive Development of Nanoscience, pp. 1, Jun. 2011.
Dente., M.D., Endovascular Repair for Aneurysm Rupture, VascularWeb, Provided by the Society for Vascular Surgery, vol. 2—2006 Issue 1.
Deffree., Nanoscale pairings of particles show promise as miniaturized power sources, pp. 16, 2011.
Edamatsu, Entangled Photons: Generation, Observation, and Characterization. vol. 46, No. 11. 2007, pp. 7175-7187.
Edwards, et al., CT measurement of main pulmonary artery diameter, 1998, pp. 1018-1020.
Esfandyari et al., Integrated smart systems with MEMS sensors, pp. 12, 2012.
Engineering a Paradigm Shift in At-Home Monitoring Devices. Jun. 2011, pp. 4 & 6.
Evans., AAA Repair: Early Intervention or Wait and See?, VascularWeb,Provided by the Society for Vascular Surgery , vol. 2—2006 Issue 3.
Grace, et al., Why MEMS-based systems solutions? Significant reasons have caused MEMS suppliers to change their design approach, thus opening new market opportunities. 2011, pp. 17-19.
Grace., What's driving MEMS commercialization 4 pgs.. 2011.
Grace., MEMS-Based Systems Solutions Emerge for Analytical Instruments, pp. 32, 2012.
Gilleo MEMS in-Medicine Aug. 2005 pp. 1-3-pp. 1-10.
Hecht, The incredible shrinking laser makes a big impact. Oct. 2011, pp. 41-45.
Hank Russell, Imaging System Tested for Visualizing Stents, VascularWeb, Provided by the Society for Vascular Surgery, vol. 2—2006 Issue 1.
Hank Russell, CT Angiography Shows Promise in Arterial Imaging, VascularWeb, Provided by the Society for Vascular Surgery, vol. 2—2006 Issue 1.
http://universe-review.ca/I08-24-scintillator.jpg.
http://www.upei.ca/~phys221/MH/How_they_work_/how_they_work_.html.
http://images.search.yahoo.com/search/images/view?frame=top&back=http%3A%2F%F%2Fs . . . .
Jayaraman, et al., 760 kHz OCT scanning possible with MEMS-tunable VCSEL. 2011, pp. 1-2.
Kastalsky, et al., Semiconductor high-energy radiation scintillation detector, pp. 650-656, 2006.
Kiourti., Biomedical Telemetry: Communication Between Implanted Devices and the External World. 2010, pp. 1-7.
Kotzara, et al., Evalution of MEMS materials of construction for implantable medical devices. 2002, pp. 2737-2750.
Lawton., Single-Use High Capacity Membrane Chromatography, pp. 30, 2012.
Lightman., Applying MEMS for quality of life, pp. 43-44, 2011.
Lesney,, Aortic Debranching Can Aid Endovascular Repair of TAA, VascularWeb, Provided by the Society for Vascular Surgery, vol. 2—2006 Issue 2.
Macneil., Stenting or Open Repair? EVAR, DREAM Trials Inconclusive, VascularWeb, Provided by the Society for Vascular Surgery ,vol. 2—2006 Issue 1.
MEMS in medical devices: the possibilities are endless. 2009, pp. 1-2.
New alloy suits MEMS devices, 3 pgs, 2012.
PEAKS of Interest, pp. 288, vol. 30, No. 4, Apr. 2012.
Reichenspurner et al., Use of the Voice-Controlled and Computer-Assistant Surgical, pp. 1, Jul. 1999.
Swift et al, Reducing Size While Improving Functionality and Safety in Next-Generation Medical Device Design, pp. 14, 2012.
Sadeg et al. Automated liquid-chromatographic analyzer used for toxicology screening in a general hospital, pp. 498-504, 1997.

\* cited by examiner

ANALYSIS AND CLEARING MODULE, SYSTEM AND METHOD

FIELD OF THE INVENTION

The field of the invention relates to, in general, medical devices and the human body. More particularly, the field of the invention relates to methods and devices with respect to the analysis of mucus, body fluid, and other material within the body: the removal of mucus, fluids, and material from the body.

BACKGROUND OF THE INVENTION

The mammalian body includes a number of subdivision systems: respiration, circulatory, lymph, gastrointestinal tract and urinary system. The lungs are the essential organs inherent within the respiration system in many air-breathing animals, including most tetrapods, a few fish and a few snails. In mammals and the more complex life forms, the two lungs are located near the backbone on either side of the heart.

The principal function of the respiratory system is to transport oxygen from the atmosphere into the bloodstream, and to release carbon dioxide from the bloodstream into the atmosphere. This exchange of gases is accomplished in the mosaic of specialized cells that form millions of tiny, exceptionally thin-walled air sacs called alveoli.

Two types of fluids move through the circulatory system: blood and lymph. The blood, heart, and blood vessels are components of the cardiovascular system. The lymph, lymph nodes, and lymph vessels are components of the lymphatic system. The cardiovascular system and the lymphatic system collectively make up the circulatory system The gastrointestinal tract refers to the stomach and intestine, and sometimes to all the structures from the mouth to the anus. (The "digestive system" is a broader term that includes other structures, including the accessory organs of digestion). The tract may also be divided into foregut, midgut, and hindgut, reflecting the embryological origin of each segment of the tract. The GI tract discharges hormones as to help control the digestion process. These hormones, including gastrin, secretin, cholecystokinin, and grehlin, are mediated through either intracrine or autocrine mechanisms, distinguishing that the cells releasing these hormones are conserved structures throughout evolution.

The main organs of the urinary system are the kidneys. This is important because the kidneys' main role is to filter water-soluble waste products from the blood. The kidneys attach at their functional endpoints to the ureters, which lie more medial and run down to the trigone of urinary bladder.

Many deaths have been reported due to the buildup of harmful substances such as: mucus, fluids and other material within the body. There is a continuing need for improvement with respect to methods of analysis and removal of the substances. More suitable systems and devices are needed for executing procedures, preferably improvements that do not require major surgery, or continued use of drugs and which may be used on higher risk patients than what conventional methods and surgery currently allows. Various devices, methods and procedures have been heretofore proposed to remove mucus, fluids, and/or other substances from diversified locations within the human body. These devices and methods include: aspirators, suction tubes and containers for insertion into a body cavity of a patient.

Particular methods have included a procedure of generating an aerosol suspension of respirable solid, dry particulate amiloride, a suctioning device is provided for use in elimination of fluid mucus. Additional methods constitute administering a physiologically acceptable salt to at least one lung of the subject in an amount effective to hydrate lung mucus secretions therein.

In U.S. Pat. No. 4,799,925, Rosenblatt illustrates an aspirator that includes two closed containers with one container having a suction tube connected to a closed bellows within the container for creating a vacuum, and the second container having a patient tube for insertion into the body cavity of a patient for sucking removal of mucus and other excess bodily fluids by the vacuum, with the two containers being connected for gaseous communication.

Ng indicates in U.S. Pat. No. 4,995,386, a suctioning device is provided for use in elimination of fluid mucus from the trachea and nostrils of a newborn infant, to prevent aspiration of such fluid into the infant's lungs before first breath. The device includes a vertically, longitudinally, upright container having a bottom wall with an opening therein to pass mucus into the container via a tubular catheter, and a top cap with an opening therein to pass suction air from the container interior toward a suction mouthpiece; a baffle or baffles in the container to intercept upward flow of mucus toward the top cap; a duct in the container to receive flow of mucus via the opening sin the bottom wall, the duct having an outlet end located to eject mucus to fall in a generally downward direction in the container, below the baffle; and a filter or filter above the duct to filter air being sucked from the container interior toward the mouthpiece via the top cap opening. The filter and one part of the baffle are typically carried by the top cap for endwise insertion downwardly into the container upper extent, the bottom wall is typically defined by a bottom cap received in the container, and the duct and a second part of the baffle are typically carried by the bottom cap for endwise insertion upwardly into lower end extent of the container.

Boucher describes a method of removing retained mucus secretions from the lungs of a human subject in U.S. Pat. No. 5,725,842. The patent denotes a method of generating an aerosol suspension of respirable solid, dry particulate amiloride, wherein said solid particulate amiloride is comprised of particles of about 1 to 5 microns, wherein said aerosol suspension is free of liquid amiloride particles; and then delivering by inhalation said aerosol suspension of respirable solid particulate amiloride to the respiratory system of said subject in an amount sufficient to achieve concentrations of amiloride on the airway surfaces of said subject of from about $10^{-7}$ to $10^{-3}$ Moles/liter, wherein the daily dose of said solid particulate amiloride is from about 1 to about 20 milligrams, and wherein said solid particulate amiloride is comprised of particles of about 1 to 5 microns, and whereby said secretions are hydrated and transported from the lung via mucociliary action.

Boucher, in U.S. Pat. No. 5,902,567, describes a method of facilitating the obtaining of a mucus sample from at least one lung of a subject comprises administering a physiologically acceptable salt to at least one lung of the subject in an amount effective to hydrate lung mucus secretions therein, and concurrently administering to said at least one lung of the subject, in an amount effective to hydrate lung mucous secretions therein, uridine triphosphate, an active analog thereof, or a pharmaceutically acceptable salt of either thereof. Pharmaceutical compositions useful for carrying out the method comprise, in combination, a physiologically acceptable salt, and uridine triphosphate, an active analog thereof, or a pharmaceutically acceptable salt of either thereof. The composition may be a liquid composition or a dry powder composition.

In U.S. Pat. No. 5,932,481, Pon describes a method for the rapid estimation of hyperplastic and hypertrophic changes in animal airways is an assay which specifically measures acidic and neutral mucoproteins in a linear fashion from 0.5 to at least 10 µg. The assay comprises exposure of a test animal to a suspected metaplastic inducer, removal of the lungs, homogenization in an appropriately buffered solution containing reducing agents and protease inhibitors; removal of particulate matter; and size-fractionation of the SDS treated soluble extract. The high molecular weight material is immobilized and stained for either acidic or neutral mucosubstances and the specific staining is quantitated. The changes observed are consistent with those seen in histological sections of the exposed tissues. The assay is useful in confirming the metaplastic potential of suspected compounds, in determining what neurohumoral mediator(s) are involved in mucus cell metaplasia in animal models for chronic obstructive pulmonary disease, and in identifying compounds which might ameliorate these effects.

In U.S. Pat. No. 5,964,223, Baran describes a nebulizing catheter system and methods of use and manufacture of an apparatus for delivering a medicine to a patient via the patient's respiratory system with control and efficiency. A nebulization catheter is positioned in the patient's respiratory system so that a distal end of the nebulization catheter is in the respiratory system and a proximal end is outside the body. In a first aspect, the nebulization catheter may be used in conjunction with an endotracheal tube and preferably is removable from the endotracheal tube. The nebulization catheter conveys medicine in liquid form to the distal end at which location the medicine is nebulized by a pressurized gas or other nebulizing mechanism. The nebulized medicine is conveyed to the patient's lungs by the patient's respiration which may be assisted by a ventilator. By producing the aerosol of the liquid medicine at a location inside the patient's respiratory system, the nebulizing catheter provides for increased efficiency and control.

Boucher describes in U.S. Pat. No. 6,022,527, a method of hydrating lung mucus secretions in the lungs of a subject in need of such treatment, comprising administering to the lungs of the subject a compound of a formula he indicates in the patent or a pharmaceutically acceptable salt thereof, in an amount sufficient to hydrate lung mucus secretions.

Boucher, in U.S. Pat. No. 6,133,247, describes a method of facilitating the obtaining of a mucus sample from at least one lung of a subject.

Boucher, in U.S. Pat. No. 6,214,536, describes a method of facilitating the obtaining of a mucus sample from at least one lung of a subject.

Shapiro, in U.S. Pat. No. 6,595,949, illustrates an automatic mucus removal device for extracting mucus from a nasal cavity includes a transportable housing which encases a compact vacuum source connected to a power source, and to which a disposable mucus trap member is removably attached. The housing includes a base portion and a barrel portion, with the mucus trap member preferably attached to one end of the barrel portion. An ejection rod is resiliently mounted to the opposing end of the barrel portion, with the ejection rod operable to expel the mucus trap member from the housing. The user therefore is not required to contact the mucus trap member or the mucus associated with it, and the mucus trap member may be disposed of or cleaned as desired.

Kumasaki, in U.S. Pat. No. 6,986,757, characterizes a suction connector, comprising a fluid passage (31) having one end to be connected to a conduit and the other end to be connected to a suction source when in use and a ventilating passage (32) branched in the middle of the fluid passage and having an opening end (33), wherein a blocking plate (34) is disposed at least at a partial region on a fluid passage side inside the ventilating passage, the cross-section of the ventilating passage is divided by the blocking plate into a plurality of regions, and fluid advancing from the fluid passage into the ventilating passage is prevented by the blocking plate from flowing out from the opening end, whereby a sucking force caused by releasing a negative pressure can be regulated sufficiently, spattering of fluid can be prevented to thus eliminate the danger of contamination and infection to an operator and assuring sanitation, and a structure is simplified.

Soltesz, in U.S. Pat. No. 6,997,918, provides methods, systems, devices and kits for performing lung volume reduction in patients suffering from chronic obstructive pulmonary disease or other conditions where isolation of a lung segment or reduction of lung volume is desired. The methods are minimally invasive with instruments being introduced through the mouth (endotracheally) and rely on isolating the target lung tissue segment from other regions of the lung. Isolation is achieved by deploying an obstructive device in a lung passageway leading to the target lung tissue segment. Once the obstructive device is anchored in place, the segment can be aspirated through the device. This may be achieved by a number of methods, including coupling an aspiration catheter to an inlet port on the obstruction device and aspirating through the port, or providing the port with a valve which allows outflow of gas from the isolated lung tissue segment during expiration of the respiratory cycle but prevents inflow of air during inspiration. In addition, a number of other methods may be used. The obstructive device may remain as an implant, to maintain isolation and optionally allow subsequent aspiration, or the device may be removed at any time.

Pivovarov, in U.S. Pat. No. 7,137,393, describes a breathing normalizer for partial insertion within the user's mouth for normalizing breathing patterns, prevention of snoring, teeth grinding, and light forms of sleep apnea. The device includes an outer plate which is positioned external to the user's mouth when in use, an elongated hollow shaft for connecting the structure to a lip plate adapted to be received between the user's lips and teeth, and a generally C-shaped multi-lobed structure adapted for receiving the user's tongue. The device is positioned within the oral cavity of the user in an operative configuration such that the tongue is retained within the multi-lobed structure, the teeth clamp down upon the connector with the lip plate positioned between the teeth and the inner portions of the upper and lower lips. The outer plate further defines a centrally disposed chamber having an inlet tube in fluid communication with the hollow tubular connector for providing an inlet for breathing air. The inlet tube is adapted for connection to a source of gas, such as oxygen, to assist in delivering the gas to the user through the lungs. In addition, the chamber includes a threaded peripheral edge adapted for threaded engagement with a container of medicine thereby facilitating the delivery of oral medications into the user's oral cavity and preferably the delivery of oral medications below the tongue. A medicine receiving chamber is further provided to allow for medicine received therein to be dispensed and/or evaporated in the user's mouth. As a result of proper application of the apparatus, breathing at night is normalized, while snoring, grinding of the teeth, and apnea are prevented, and medications may be simultaneously delivered orally.

Johnson, in U.S. Pat. No. 7,204,252, describes a system, device or method uses surface energy to assist in fluid transport or separation. One example includes removing mucus from a subject's lungs during mechanical ventilation of the subject using a tracheal tube. At least one wicking fluid pickup port is located more distal or more proximal than a sealing device between the tracheal tube and the trachea. Surface energy assists in introducing mucus into the port. A peristalsis or other pump is used to remove from the subject the wicked-in liquid. Ventilation is not impaired by the mucus removal.

Johnson, in U.S. Pat. No. 7,278,429, describes systems, devices, and methods for using surface energy to assist in fluid transport or separation. One example includes removing mucus from a subject's lungs during mechanical ventilation of the subject using a tracheal tube. At least one wicking fluid pickup port is located more distal than a sealing device between the tracheal tube and the trachea. Surface energy assists in introducing mucus into the port. A peristalsis or other pump is used to remove from the subject a substantially contiguous column of the wicked-in liquid. Ventilation of the subject is not impaired by the mucus removal. Safety venting reduces or avoids damage to tissue occluding the port. Other structures may assist in directing the mucus toward the port. Various illustrative examples include single lumen tracheal tubes, double lumen tracheal tubes, two-piece tracheal tubes (having outer and inner cannulas) and bronchial blockers. This document also discusses several other exemplary applications, such as oil/water separation, transportation of a lubricant to a drill bit tip, waste separation and/or solidification.

Boyer, in U.S. Pat. No. 7,851,456, describes an invention is directed to a method of enhancing or facilitating the clearance of the lung mucus secretions in a subject. This invention is also directed to a method of facilitating the hydration of the lung mucus secretions in a subject. This invention is further directed to a method of preventing or treating diseases or conditions associated with impaired lung or airway function in a human or other mammal.

Guiliguian, in U.S. Pat. No. 7,929,741, describes a method for detecting and localizing mucus plugs in digitized lung images, includes providing a digitized lung image volume comprising a plurality of intensities corresponding to a 3-dimensional grid of points, extracting a bronchial tree from said lung image, said bronchial tree comprising a plurality of branching airways terminating at terminal points, providing a model of a 2-dimensional cross section of an airway, selecting an extended point beyond a terminal point of an airway branch in a direction of said airway branch, obtaining a 2-dimensional cross section I of size m×n points from said lung image about said selected point, processing said 2-dimensional cross section I by calculating a local neighborhood function for each point in the cross section and forming a union of all local neighborhood functions, and calculating a correlation between processed 2-dimensional cross section and said airway model, wherein said correlation is indicative of the presence of a mucus plug within said airway.

Danek describes in U.S. Pat. No. 7,938,123, a method for decreasing responsiveness or decreasing resistance to airflow of airways involves the transfer of energy to or from the airway walls to prevent or reduce airway constriction and other symptoms of lung diseases. The treatment reduces the ability of the airways to contract during an acute narrowing of the airways, reduces mucus plugging of the airways, and/or increases the airway diameter. The methods

SUMMARY OF THE INVENTION

In one aspect of the present invention, a module for insertion into a living body is provided that includes: an instructions receiver configured to receive wireless transmissions of instructions from a master controller located outside of the body when the module is inside the body; an energy receiver configured to receive wireless transmission of non-destructive energy from the master controller located outside of the body when the module is inside the body; an energy converter configured to convert the non-destructive energy received to destructive energy; and an energy emitter configured to emit the destructive energy.

In at least one embodiment, an opening is provided in a surface of the module, the opening communicating with a chamber within the module.

In at least one embodiment, the module includes a negative pressure generator configured to generate negative pressure in the chamber to draw material in the body into the chamber.

In at least one embodiment, the module includes a liquid chromatography analyzer configured to analyze the material drawn into the chamber.

In at least one embodiment, the module includes a camera configured to capture images of the body when the module is inserted in the body, wherein the module wirelessly transmits the images to the master controller outside the body.

In at least one embodiment, the module includes a battery configured to provide backup power to the module.

In at least one embodiment, the module includes a gate, the gate being movable from an open position allowing the opening to communicate with the chamber, to a closed position wherein the opening is closed off, the gate being also movable from the closed position to the open position.

In another aspect of the present invention, a module for insertion into a living body is provided that includes: an instructions receiver configured to receive wireless transmissions of instructions from a master controller located outside of the body when the module is inside the body; an opening in a surface of the module, the opening communicating with a chamber within the module, the opening and the chamber being configured and dimensioned to receive material from inside the body when the module is inserted into the body; an analyzer configured to analyze composition of the material received in the chamber; and a transmitter configured to wirelessly transmit composition analysis results produced by the analyzer to the master controller.

In at least one embodiment, the analyzer includes a liquid chromatography analyzer.

In at least one embodiment, the module includes a negative pressure generator configured to generate negative pressure in the chamber to draw the material into the chamber.

In at least one embodiment, the module includes a gate, the gate being movable from an open position allowing the opening to communicate with the chamber, to a closed position wherein the opening is closed off, the gate being also movable from the closed position to the open position.

In at least one embodiment, the module includes an energy receiver configured to receive wireless transmission of non-destructive energy from the master controller located outside of the body when the module is inside the body; an energy converter configured to convert the non-destructive energy received to destructive energy; and an energy emitter configured to emit the destructive energy.

In another aspect of the present invention, a system for treatment of a condition within a living body is provided that includes: a master controller located outside of the body; and a module configured and dimensioned to be introduced into at least one of a body cavity, duct or vessel, and to be guided and driven through the at least one of a body cavity, duct or vessel by wireless forces and communication from the master controller.

In at least one embodiment, the master controller drives the module using magnetic forces.

In at least one embodiment, the module includes at least one camera configured to wirelessly transmit images from within the at least one of a body cavity, duct or vessel to the master controller to aid guidance of the driving of the module.

In at least one embodiment, the module includes at least one guide element detectable by the master controller to aid guidance of driving of the module.

In at least one embodiment, the module includes a module instructions receiver and the master controller comprises a master instructions transmitter, the master instructions transmitter configured to transmit wireless instructions to the module instructions receiver when the master controller is located outside of the body and the module is inside the body; and the module comprises a module transmitter and the master controller comprises a master receiver, the module transmitter configured to transmit wireless transmissions to the master transmissions receiver when the master controller is located outside of the body and the module is inside the body.

In at least one embodiment, the master controller includes a non-destructive energy generator and a non-destructive energy transmitter, and the module comprises a non-destructive energy receiver configured to receive non-destructive energy transmitted by the non-destructive energy transmitter when the master controller is located outside of the body and the module is inside the body.

In at least one embodiment, the module includes an energy converter configured to convert the non-destructive energy received to destructive energy; and an energy emitter configured to emit the destructive energy.

In at least one embodiment, the module includes an opening in a surface of the module, the opening communicating with a chamber within the module; a negative pressure generator configured to generate negative pressure in the chamber to draw material in the body into the chamber; and an analyzer configured to analyze composition of the material drawn into the chamber; wherein the module is configured to wirelessly transmit analysis results of the material by the analyzer to the master controller.

In another aspect of the present invention, a method of treating the body is provided that includes: inserting a module into a duct, vessel or cavity of the body of a patient; moving and guiding the module through the anatomy of the patient to a target location, wherein the moving and guiding are performed by wireless application of forces to the module by a master controller located outside of the body; and performing a treatment on material in the body at the target location.

In at least one embodiment, the moving and guiding are performed by a nuclear magnetic resonance machine of the master controller.

In at least one embodiment, a plurality of the modules are moved and guided by the master controller within one or more ducts, vessels or cavities, and at least two of the modules are moved and guided either serially or in parallel.

In at least one embodiment, the treatment performance comprises analyzing material from the target location.

In at least one embodiment, the treatment performance comprises drawing material from the target location into a chamber in the module.

In at least one embodiment, the method includes analyzing composition of the material in the chamber.

In at least one embodiment, the method includes destroying the material.

In at least one embodiment, the destroying comprises vaporizing the material.

In at least one embodiment, the treatment performance comprises destroying material from the target location.

In at least one embodiment, the destroying comprises vaporizing the material.

In at least one embodiment, the module includes at least one camera, and the method further comprises capturing an image by the at least one camera and wirelessly transmitting the image to the master controller.

These and other features of the invention will become apparent to those persons skilled in the art upon reading the details of the modules, systems and methods as more fully described below.

DETAILED DESCRIPTION OF THE INVENTION

Figure 1:
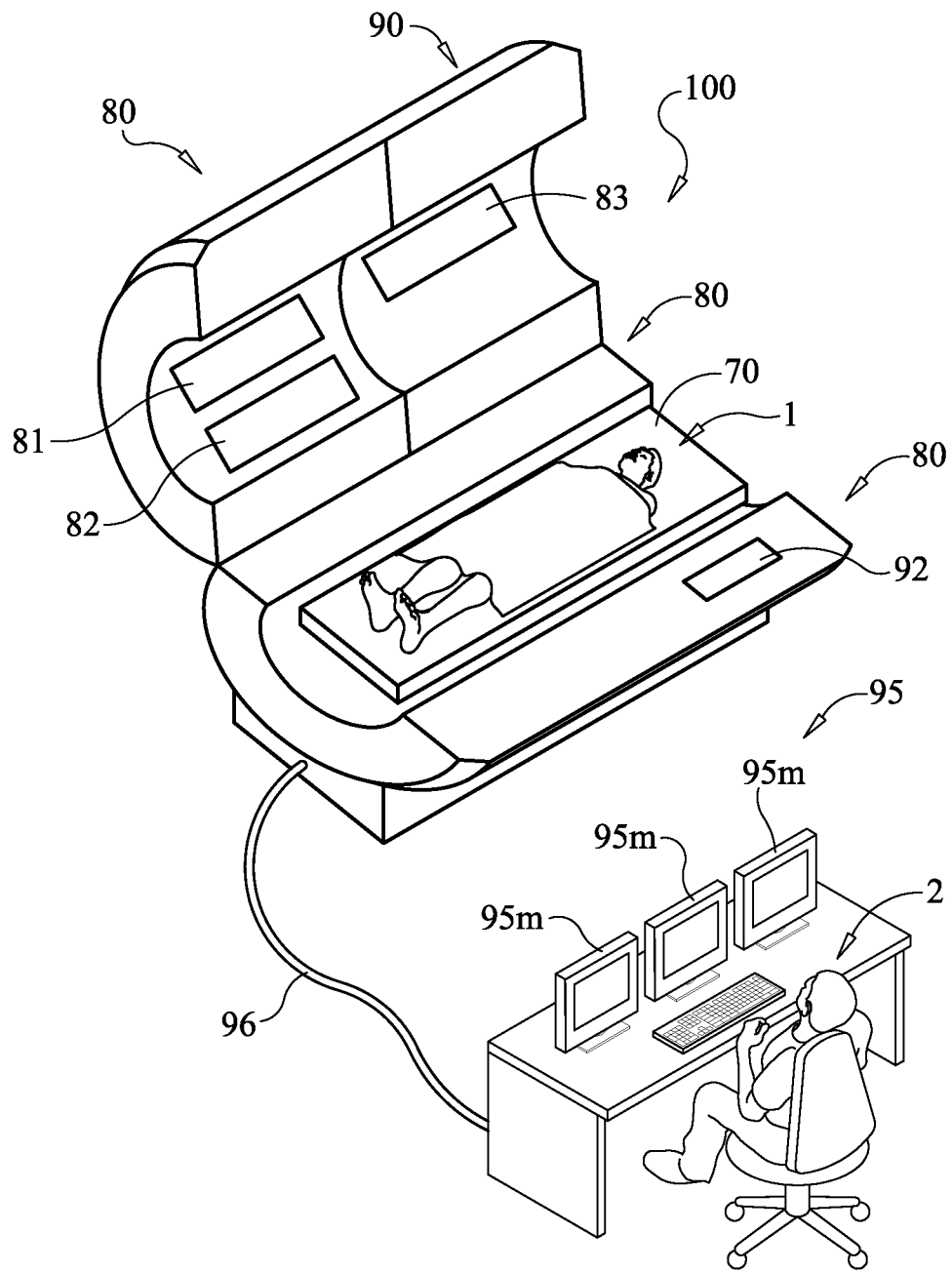
FIG. 1 schematically illustrates a master machine and patient according to an embodiment of the present invention.

Before the present systems, in which devices and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a beam transmission unit" includes a plurality of such beam transmission units and reference to "the device" includes reference to one or more devices and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

The term "patient" herein refers to a human patient who may be an adult or child, male or female. Further, the term patient, as used herein, includes mammalian species of all types, genders and developmental stages.

"Nanotechnology" generally refers to technology relating to structures sized between about 1 to about 100 nanometers in at least one dimension, and involves developing materials or devices within that size. Quantum mechanical effects are very important at this scale. Nanotechnology is very diverse, fluctuating from enlargement of conventional device physics to completely new approaches based upon molecular self-assembly, from flourishing new materials with dimensions on the nanoscale to exploring whether one can directly control matter on the atomic scale. Nanotechnology may be able to create many new materials and devices with a vast range of applications, such as in medicine, electronics, biomaterials and energy production.

"Micro-Electro-Mechanical Systems" (MEMS), involves the integration of mechanical elements, sensors, transducers, actuators, and electronics on a common silicon substrate through microfabrication technology. While the electronics are fabricated using integrated circuit (IC) process sequences (e.g., CMOS, Bipolar, or BICMOS processes), the micromechanical components are fabricated using compatible "micromachining" processes that selectively etch away parts of the silicon wafer or add new structural layers to form the mechanical and electromechanical devices. Microelectromechanical systems (MEMS) (also written as micro-electro-mechanical, MicroElectroMechanical or microelectronic and microelectromechanical systems) is the technology of very small mechanical devices driven by electricity; it merges at the nano-scale into nanoelectromechanical systems (NEMS) and nanotechnology.

MEMS are made up of components between 1 to 100 micrometers in size (i.e. 0.001 to 0.1 mm) and MEMS devices generally range in size from 20 micrometers (20 millionths of a meter) to a millimeter. They usually include a central unit that processes data, the microprocessor and several components that interact with the outside such as microsensors. The following materials have been used to construct MEMS devices, single crystal silicon (Si), poly-crystalline silicon (polysilicon), silicon oxide (SiO2), silicon nitride (Si3N4), single crystal cubic silicon carbide (3C—SiC or b-SiC), titanium (Ti).

An "integrated circuit" (IC) is an electronic circuit manufactured by the patterned diffusion of trace elements into the surface of a thin substrate of semiconductor material. Integrated circuits (IC) are constructed of semiconducting materials, which are midway between good conductors, like copper, and insulators such as plastic. Silicon is the current favorite. Ultrapure silicon is mixed with small, precise amounts of other elements to create electronic materials with different characteristics. Additional materials are deposited and patterned to form interconnections between semiconductor devices. The integrated circuit (IC) is one of the most complex things ever made. Integrated circuits may be small squares of silicon, imprinted with microscopic patterns. The patterns may contain hundreds of millions of transistors, resistors and other electronic parts.

"Nuclear Magnetic Resonance" (NMR) was described independently by Felix Bloch and Edward Mills Purcell in 1946, both of whom shared the Nobel Prize in physics in 1952, for their discovery. The development of NMR as a technique of analytical chemistry and biochemistry parallels the development of electromagnetic technology. This technique allows the detection of radio frequency energy, and on the absorption of such energy by matter.

"Computerized Axial Topography (CAT)/CT (computed tomography), sometimes called CAT scan, uses special x-ray equipment to obtain image data from different angles around the body and then uses computer processing of the information to show a cross-section of body tissues and organs. Recent technical advances with respect to CT scanners now enable 192 images of the body per second. This non-invasive, virtually pain-free procedure offers exceptional image quality, which can mean better diagnosis, faster recovery time and increased patient comfort and convenience.

"Internet Protocol Packet" (IP Packet) is the smallest message entity exchanged via the Internet Protocol across an Internet Protocol version 6 (IPv6) network. Packets consist of control information for addressing and routing, and a payload consisting of user data. The control information in IPv6 packets is subdivided into a mandatory fixed header and optional extension headers. The payload of an IPv6 packet is typically a datagram or segment of the higher-level Transport Layer protocol, but may be data for an Internet Layer (e.g., ICMPv6) or Link Layer (e.g., OSPF) instead.

"Magnetic Resonance Imaging" (MRI) is a unique imaging method because, unlike the usual radiographs (x-rays), radioisotope studies or even Computed Tomography (CT) scanning, it does not rely on ionizing radiation. Instead radio frequency waves are directed at protons, the nuclei of hydrogen atoms, in a strong magnetic field. The protons are first "excited" and then "relaxed," emitting radio signals that can be computer-processed to form an image. In the body, protons are most abundant in the hydrogen atoms of water—the "H" of $H_2O$—so that a MRI image shows differences in the water content and distribution in various body tissues.

"Nuclear Scans": in some instances, a doctor may request that someone have a nuclear scan. A nuclear scan involves only a small "tracer" dose of radioactive material, and is not dangerous. Once this tracer element is injected into a patient's system, it can be followed through the system as the patient lies directly underneath a sensing device. A nuclear scan is most often used to assess body function. Other uses include measurement of stomach emptying and localization of intestinal bleeding. Nuclear scans require very little preparation.

A "laser" device is a device that emits light (electromagnetic radiation) through a process of optical amplification based on the stimulated emission of photons. The term "laser" originated as an acronym for Light Amplification by Stimulated Emission of Radiation. The emitted laser light is notable for its high degree of spatial and temporal coherence, unattainable using other technologies. Spatial coherence typically is expressed through the output being a narrow beam which is diffraction-limited, often a so-called "pencil beam." Laser beams can be focused to very tiny spots, achieving a very high irradiance. Or they can be launched into a beam of very low divergence in order to concentrate their power at a large distance.

"Chromatography" is a technique used to analyze mixtures and substances. Chromatography can be used to monitor the progress of a reaction, identify compounds present in a given mixture, and determine the purity of a substance. Since the 1950s, gas chromatography (GC) has been a common approach for analysis of volatile mixtures in which the components are differentiated in space and time. Conventional GCs tend to be large, fragile, and relatively expensive table-top instruments with high power consumption, but they are known to deliver accurate and selective analysis. The use of MEMS technology for GC development is a promising approach to micro-instruments having lower cost, smaller size, lower power consumption, faster analysis, and greatly increased portability for in-field use. Such systems will make gas chromatography a pervasive method for analysis, with applications related to biomedical diagnostic procedures.

"X-radiation" (composed of X-rays) is a form of electromagnetic radiation. X-rays have a wavelength in the range of 0.01 to 10 nanometers, corresponding to frequencies in the range 30 petahertz to 30 exahertz ($3\times10^{16}$ Hz to $3\times10^{19}$ Hz) and energies in the range 120 eV to 120 keV. They are shorter in wavelength than UV rays and longer than gamma rays. In many languages, X-radiation is called Röntgen radiation, after Wilhelm Conrad Röntgen, who is usually credited as its discoverer, and who had named it X-radiation to signify an unknown type of radiation.

Recently uncovered archival evidence shows that the original discoverer of X-rays was a Ukrainian physicist Ivan Pulyui, who worked in Vienna together with Röntgen and shared the results of his work with him Correct spelling of X-ray(s) in the English language includes the variants x-ray(s) and X ray(s). XRAY is used as the phonetic pronunciation for the letter x. X-radiation used in the present invention is "non-destructive X-radiation" (X-ray energy) that doesn't significantly destroy or damage human tissue, such as the X-ray energy typically used for performing chest X-ray imaging, dental imaging, fluoroscopy and the like.

"Destructive energy" as used herein, refers to energy, such as laser energy, RF energy, microwave, cryogenic, ultrasound or other mode of energy applied at wavelength, power and/or time configured to damage or destroy human tissue, for example for ablating an obstruction within a vessel, ablation of a tumor, etc. Destructive energy is applied to damage, vaporize or destroy patient tissue.

"Beam transmission/clearing energy", as used herein, refers to destructive energy used to destroy, ablate, vaporize or otherwise remove tissue. This is distinguished from non-destructive energy such as X-rays (as used herein) and wireless communication signals, for example.

"Guide, control instructions RF energy", as used herein, refers to wireless RF signals used to control a module as described herein. For example, wireless RF instructions can be sent from a master NMR machine instruction transmitter to an instruction receiving unit of a module.

Two broad types of energy are referred to: destructive energy (examples of which include, but are not limited to beam transmission/mucus clearing energy) and nondestructive energy (examples of which include, but are not limited to control instructions).

DETAILED DESCRIPTION

The present invention provides embodiments that overcome shortcomings of the prior art by using one or more advanced technologies, including semiconductor-manufacturing methodology, nano-manufacturing techniques to produce an internal mucus clearing and analysis module. After inserting the module into a patient's body, the invention allows the detection of the mucus clearing and analysis module, and controlling, positioning and guiding the module within a duct, vessel, organ or surgical target by means of a Nuclear Magnetic Resonance (NMR) control system. Accordingly, a system that provides for the detection, control and positioning of a module within the duct, vessel, organ or cavity is provided. The present invention relates to the medical analysis of diseases, mucus or impediments, and particularly to detection and analysis of vulnerable material within the ducts, cavities, vessels, or other body sub-systems. The invention provides methods of detection and elimination of harmful accumulations within the human body's sub-systems, as well as ducts, vessels, organs, and/or cavities within the human body and the elimination of these harmful accumulations.

Various embodiments of the present invention include one or more of manufacturing of the device (module), the detection of the module, guiding and controlling, positioning and using the module to clear the vessel by means of a Nuclear Magnetic Resonance (NMR) control system. Within the scope of at least one embodiment of the present invention, a module is produced, allowing for computer-assisted surgery of the procedure within the duct, vessel cavity, or organ to be surgically targeted. The vessel-clearing module will be controlled and guided by a method described by Zurn in U.S. Patent Application Publication No. US 2009/

0062639 A1, filed on Aug. 27, 2007, which is hereby incorporated herein, in its entirety, by reference thereto.

A module such as described according to an embodiment of the present invention can be used in many medical applications. As mentioned, it may be employed in miscellaneous types of ducts, vessels, organs, and cavities within the human body. The invention can be used to sustain and to eliminate pathological body sub-system deficiencies.

According to at least one embodiment of the present invention, a biocompatible MEMS module, is assembled, including: a communication element configured to receive radio frequency energy from a source external of the device; radio frequency receiving unit; a communication link between the communication element and each of the MEMS device regions.

According to at least one embodiment of the present invention, a module may be constructed using nanotechnology to create a microelectromechanical device (MEMS). Each module may have different dimensions, such as dimensions of (100×100×50 microns): smaller modules will be used for smaller targeted areas of the sub-systems of the body. The size of the module is determined, at least in part, by the inside diameter of the duct, vessel, and cavity in need of the analysis and of the substance removal procedure.

Figure 3A:
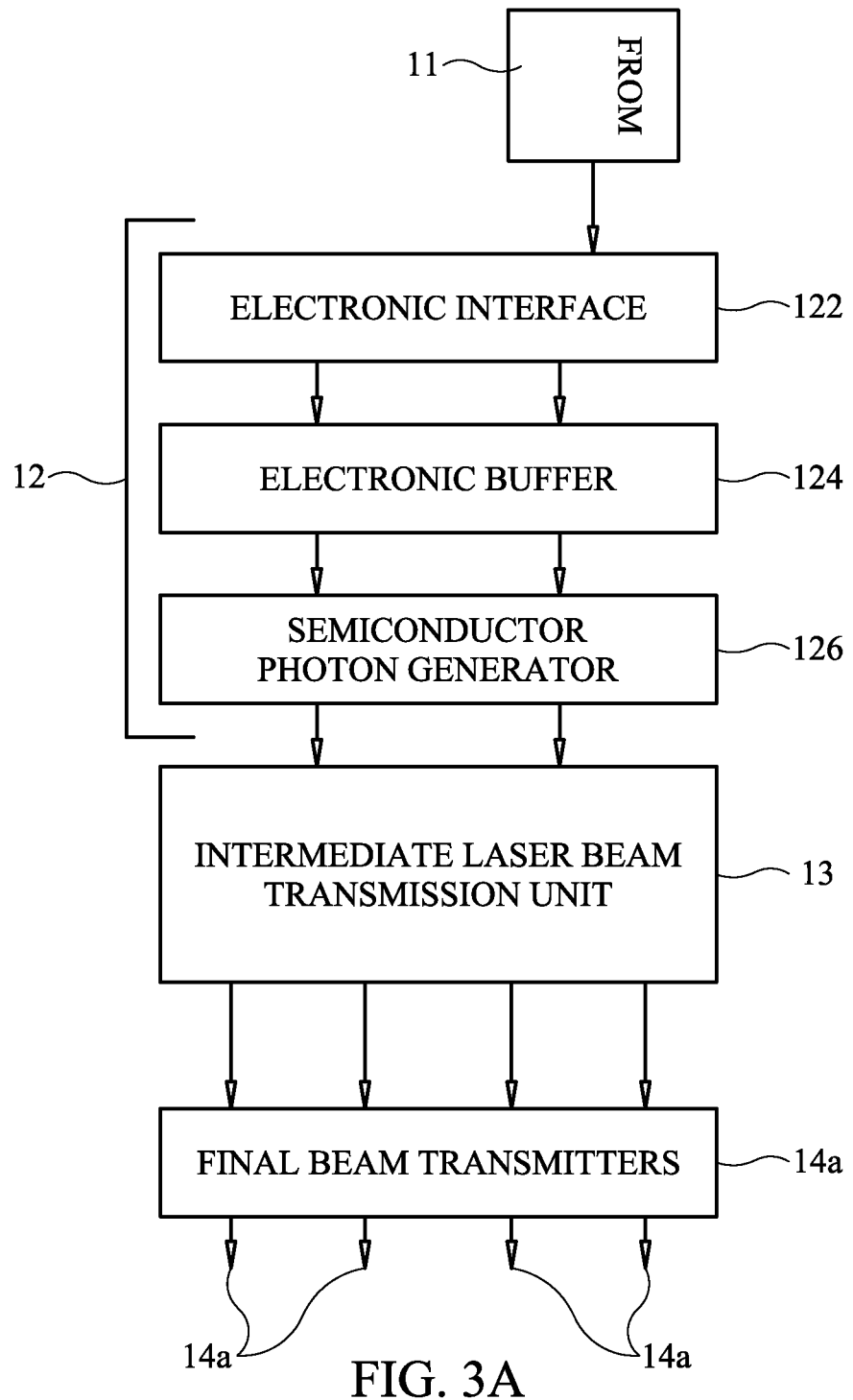
FIG. 3A is an expanded block diagram indicating an electronic interface, electronic buffer and semiconductor photon generator indicating additional circuits within an x-ray energy conversion section, according to an embodiment of the present invention.

According to at least one embodiment of the present invention, the module includes the following sections: wireless instructions transmit/receive unit 19, X-ray receiving unit 11, X-ray energy conversion unit 12 (which includes additional circuits illustrated in FIG. 3A). Also included in the module, according to at least one embodiment, are an intermediate laser beam transmission unit 13, multiple final beam transmitter units 14a in beam length and intensity unit 14 and guide and transducer bar 17. Guide and transducer bar includes communication circuits (bus) connecting to all sections within the module 10. Further included within the module 10, according to at least one embodiment of the present invention, are positioning elements 15. Transmit/receiving unit 19 also transmits real time information from module 10 to the master machine 100.

According to at least one embodiment of the present invention, the module includes the following sections: vaporizer chamber 30, analysis chamber 23 and input/output chamber 22. Further included in the module are multiple gates 24.

According to at least one embodiment of the present invention, two types of energy are sent to module 10 from master machine 100: wireless instruction signals are sent to section 19 to guide and control the movement of the module 10, and X-ray energy is sent to section 11 which is converted into destructive laser energy in the module 10. The wireless instructions are received by the wireless instruction transmit/receiving unit 19 and are then transmittable via the communication links (paths) within 17 to other module subsections within the module 10. The guide and control wireless instructions are in the form of information packets. The X-ray energy is converted to laser beams to remove the blockage.

According to at least one embodiment of the present invention, module 10 receives two types of non-destructive energy: X-ray and wireless instructions (e.g., in the form of RF energy). The X-ray energy is converted to destructive energy in the form of laser energy. The wireless instructions are used for guiding and controlling module 10 according to an embodiment of the present invention. The non-destructive energy is supplied to the module from a source outside of the patient's body, e.g., from a NMR machine or other controller. The X-rays are within a voltage range of about 12 to about 120 keV (0.10 to 0.01 nm wavelength), and are applied in short duration not harmful to the human body. The wireless Instructions are provided as RF energy conforming to IEE 802.11 standards used in implementing wireless local area network (WLAN) computer communications in the 2.4, 3.6 and 5 GHz frequency bands.

According to at least one embodiment of the present invention, X-ray energy, received by the X-ray receiving unit 11, is converted to laser energy by the X-ray conversion unit 12 and used to deliver a laser beam as the beam transmission vaporizing energy (destructive energy) that will be used in the beam transmission section, described below, to destroy/vaporize the substance, mucus, fluid, material within the vaporizing chamber such as when collected within the vessel, duct, cavity or organ. The intermediate beam transmission section 13 transmits laser energy in the form of a laser beam, through the final beam transmitters 14a (e.g., see FIG. 3), vaporizing the substance to be destroyed. The intermediate laser beam transmission unit 13 transmits the laser beam energy to the multiple final laser beam transmitters 14a in section 14.

Coded wireless instructions (guide and control signals) may be sent to the module 10 to guide and control it. The instructions are sent from an instruction transmit/receiving unit 83 outside the patient's body to an instruction transmit/receiving unit 19 of the module inside the patient's body. Instructions are sent within a packet string in either direction. The method of delivery of the instructions is similar to the Internet Protocol packet. The packet contains header, body and trailer information that is decoded by the MEMS module for controlling functions of the module. The instructions are sent from a down link transmission unit (within the NMR section), received, then decoded within the clearing module and processed. The instructions are executed by the module to guide and control the module to perform the necessary procedures.

In at least one embodiment of the present invention, data transmission from a MEMS clearing module, referred to as an uplink transmission, transmits to a master NMR information which is necessary for fine tuning adjustments with respect to the sensors, guide circuitry and beam transmission. This allows for "real time" feedback to control the motion and beam transmission within the MEMS module. Data transmission from the NMR, referred to as a downlink transmission, transmit information to the MEMS clearing module necessary for controlling the sensors within the beam transmission section and guide circuitry. This data from the NMR may adjust sensing activities, guide activities, and beam transmission of the MEMS module as alternating conditions occur.

Wireless instruction signals, used to guide and control the module, are transmitted to section (19) and X-rays are transmitted to section (11) which are converted into laser beam destructive energy to vaporize the substance. Wireless instructions are sent in a structured method (packet steam), whereas X-rays are transmitted and converted to beam transmission energy.

In at least one embodiment of the present invention, a beam transmitting sub-section contains four transmit elements, each with its own independent intensity and beam length controls. The beam transmitting subsections comprise MEMS tunable (adjustable) lasers, each with a variable wavelength adjustable beam. The control signals for operating the beams transmitting subsections are wireless instructions received by section (19) from the master machine 100 outside of the patient.

Nuclear Magnetic Resonance (NMR) techniques are used for positioning and guiding the module(s) according to an embodiment of the present invention during a procedure on a patient. Precise movement of the module is critical to avoid damaging a cavity, duct, organ or vessel wall or any other human tissue that is not intended to be destroyed or removed during the procedure.

Modules according to the present invention are made of material tolerated by the human body, and can be applied within tubes, cavities, blood vessels and/or ducts in the body of a living animal, a living human or some other intricate accessible place within either. Modules can comprise a resilient flexible substance substantially inert to bodily fluids (e.g., silicone, or other biocompatible polymer having similar properties).

In at least one embodiment of the present invention, a buffer transducer and guide sub-section of the module contains MEMS sensors that control the module in relationship to contact with the cavity, duct or vessel wall tissue. The sensors also permit differentiating between different levels of rigidity in cavity, duct or vessel wall tissues. The sensors contain ultrasound transducers that are configured to differentiate between duct, cavity and/or vessel wall tissue versus obstructive tissue, see also U.S. Pat. No. 7,967,754 and Guest Editorial, "Fantastic voyage through the cardiovascular system", Eur J. Echocardiography (2004) 5, 8-11, both of which are hereby incorporated herein, in their entireties, by reference thereto.

In at least one embodiment of the present invention, at least one, preferably a plurality of cameras are employed with-in the module. The camera(s) give(s) the operator, controlling the module, a visual representation of the relationship of the module's location relative to the surgical target.

Integration of transducers, sensors, actuators, and other microstructures within the electronics of a module, according to an embodiment of the present invention, provides the ability to transform medicine and surgery from surgery by skilled doctors, to computer assisted surgery by skilled technicians or engineering personnel.

Methods of positioning modules are provided, using a Nuclear Magnetic Resonance (NMR) control system to monitor the positioning of the modules. In at least one embodiment, positioning and guiding of a module is facilitated by provision of a small "tracer" dose of radioactive material that is not hazardous to the patient that it is inserted into. Once the module with the tracer element is injected into the vessel, duct or cavity, the NMR system can directly track the location of the module at all times.

Sensor features of the module measure quantities of pressure and/or hardness of the cavity, duct or vessel walls. These sensing features allow real time feedback, for use in guiding and positioning the module. The real time feedback allows proper positioning and movement of the module to effectively operate without damaging cavity, duct or vessel walls.

Tunable lasers used in the vaporizing chamber can be adjusted as to the wavelength of light emitted. In at least one embodiment, the wavelength is about 1310 nm, with a range of 110 nm, i.e., a range of from about 1255 nm to about 1365 nm preferred, although the present invention is not limited to this range.

Modules, methods and systems described herein may alternatively be used to clear ducts, vessels, cavities of mucus or other substances; as well as to treat other difficult to approach places within the patient's body. For example, modules according to embodiment of the present invention may be used to treat other structures in, but not limited to the respiratory, biliary, or urinary tracts to clear mucus or substances.

Turning now to FIG. 1, an automated mucus clearing system 100 is schematically shown. A patient 1 is positioned on a table 70, with elements of an NMR (nuclear magnetic resonance) machine 80 below and above him/her. The patient 1 is almost fully enclosed by the CT/MRI (computerized tomography/magnetic resonance imaging) equipment 90 and NMR 80 machines. The top of the system 100 has a clamshell arrangement/configuration with the forward portion 90 containing CT/MRI equipment, which, in combination with NMR equipment 80 in the lower portion of system 100 is configured to perform nuclear magnetic resonance functions. Both CT/MRI and NMR machinery are currently available as known to those of ordinary skill in the art. The upper clamshell is configured to move back and forth (forwardly and rearwardly) over the patient 1 in directions toward the head (forward) and the feet (rearward) of the patient 1, so that either portion 80 or 90 can be located over any desired location of the patient 1. These elements of the system 100 allow control of the mucus clearing module 10 (schematically illustrated in FIG. 2a) during guiding and control thereof and provide RF energy and communication information and transmit the same to the mucus clearing modules 10.

Figure 2A:
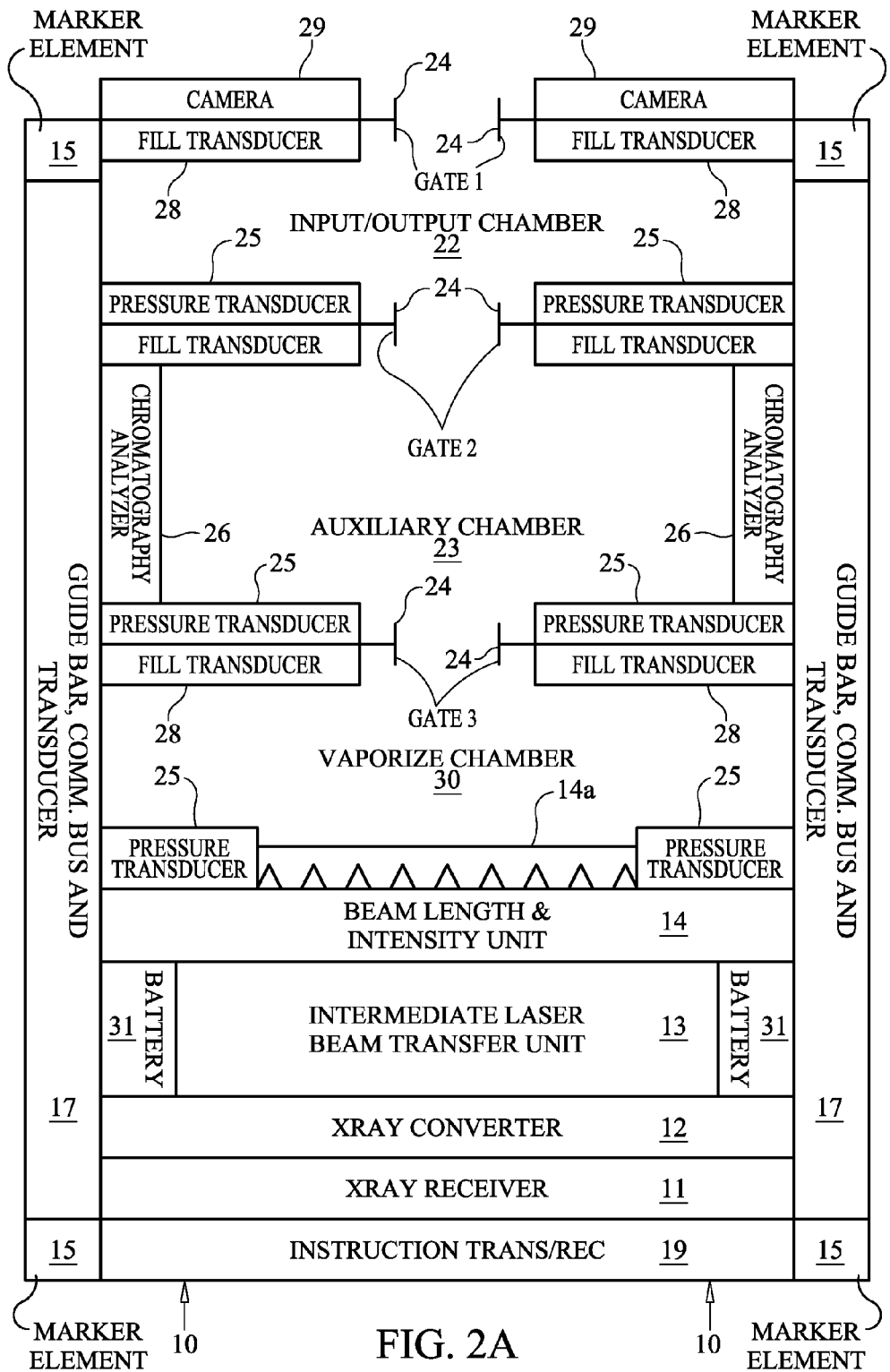
FIG. 2A is a schematic illustration of a biocompatible mucus analysis and clearing module according to an embodiment of the present invention.

FIG. 2A is a schematic illustration of a biocompatible mucus clearing module 10 according to an embodiment of the present invention. In at least one embodiment, module 10 comprises a MEMS device. Module 10 is fabricated using a combination of MEMS technology and integrated circuit technology. Module 10 includes multiple sub-sections/units. The X-ray receiving sub-section/unit 11 receives non-destructive X-ray energy from the X-ray transmitting module 82, which transmits the X-ray energy emitted by X-ray generation unit 81. Transmitting module 82 is focused on the module 10 and then emits the X-rays in a focused delivery to module 10, where they are received by receiving unit 11. X-ray energy conversion unit 12 converts the X-rays received by X-ray receiving unit 11 to laser energy. As indicated in FIG. 3A, the X-rays from receiving unit 11 are sent through the electronic interface 122 of X-ray energy conversion unit 12 through electronic buffer 124 and to semiconductor photon generator 126 which generates photons therefrom. X-ray energy conversion unit 12 then outputs the photons to intermediate laser beam transmission unit 13. The X-rays are converted to an electronic signal by the electronic interface 122 that is buffered through buffer 124 and sent as an input to the photon generator 126. The X-ray energy conversion unit 12 converts the non-destructive X-ray energy received by X-ray energy receiving unit 11 to energy that is transmitted by use of the intermediate beam transmission unit 13. As shown in FIG. 3a, the X-ray energy conversion unit 12 includes an electronic interface 122 that converts the frequency of the X-rays received from X-ray receiving unit 11, and inputs an electronic signal to the semiconductor photon generator 126, where the electronic signal is converted to photons.

The X-ray conversion unit 12 also converts X-rays, utilizing the electronic interface (122), and the electronic buffer (124) used to power various sub-sections within the module (10). The electronic power from the electronic buffer is connected to the guide bar, communications bus and transducer (17). The electronic power is distributed within the unit (17) to provide power to sub-sections such as: module battery (31) chromatography analyzer (26), pressure transducer (25), fill transducer (28), and instruction receiver (19).

The module battery (31) powers the module (10) in case of emergency power needs or short term power disruptions. The module battery (31) is charged using the electrical energy from unit (12) by the electronic interface (122) and the electronic buffer (124) after conversion of the X-rays.

The intermediate laser beam transmission unit 13 prepares the photons received, splits the single channel of photons into multiple channels of photons, in this example, four channels of photons and transfers this destructive energy to the final beam transmitters 14a in beam length and intensity unit 14. The photons within unit 13 are split by the circuitry within the intermediate laser beam transmission unit 13 and then fed to unit 14. The final beam transmitters 14a in beam length and intensity unit 14 emit focused laser beams resulting from the commutation of the circuits between the electronic interface 122 and the final beam transmitters 14a, the circuits of which condition the laser beam outputs.

The circuits between 122 and 14a condition the beams by means of on/off switches that allow bursts, variations in the electronic inputs to the circuits between 122 and the final beams transmitters' outputs that control the intensity of the beams and length of the beams. The intermediate 13 and final 14a beam transmitters also act as coarse and fine adjustments to the laser beams outputted. The beam length and intensity unit 14 contains multiple elements 14a which are the final beam transmitters (four elements 14a in the embodiment of FIG. 2A, although more or fewer can be employed, even just one). Each element 14a is individually controllable to vary wavelength of the destructive energy emitted therefrom in a manner described above. Each element 14a is also individually controllable as to time of emission, burst length, amount of emission, etc. Each element 14a is also individually controllable as to orientation, such that the direction of aim of emission of the laser beam from each can be individually controlled, thereby providing localized beam control.

A buffer/transducer/guide bar/communication bar 17 is provided on two opposite sides of module 10 as illustrated in FIG. 2A. Redundancy is provided by providing a pair of bars 17 to ensure optimum functioning whether either the right side or left side of the module 10 is in contact with a duct wall, cavity or vessel wall. Instruction receiving unit 19 receives control signals in the form of wireless RF signals, from the instruction transmission module 83 of CT/MRI section 90. The instruction transmission module 83 is a subsection of the top clam shell 90. The top clam shell contains X-ray generation module 81, X-ray transmission module 82 and instruction transmission module 83. Instruction transmission module 83 sends instructions to guide and control the module 10. Instruction receiving unit 19 receives the instructions from module 83 and transfers the instructions to the various units (11, 12, 13, 14, 15, 17, 24, 25, 26, 29, etc) of module 10. Thus, instruction receiving unit 19 has multiple functions, in that it not only sends guide and control instructions to Guide Bar and Communications Interface bars 17, but it also sends instructions to control the activities within the sub-sections of the module 11, 12, 13, 14, 15, 17, 24, 25, 26, 29, etc). The communication link within the buffer/transducer of the guide bar and communication interface 17 is a computer bus structure that links all of the units (11, 12, 13, 14, 15, 17, 24, 25, 26, 29, etc) in communication with the instruction transmit/receiving unit 19. The X-ray transmitting module 82 sends X-ray energy (non-destructive) to X-ray receiving unit 11 and the instructions transmission module 83 send wireless instructions energy (non-destructive) to instruction receiving unit 19.

At the front of the module, one or more cameras 29 may be employed within the module 10. The cameras give the operator, controlling the module, a visual representation of the relationship of the module's location relative to the surgical target.

Pressure transducers (25) function as vacuum pumps to provide negative pressure to draw in the substance, mucus, and material for analysis or to vaporize the substance, mucus, material within the various chambers.

Figure 2B:
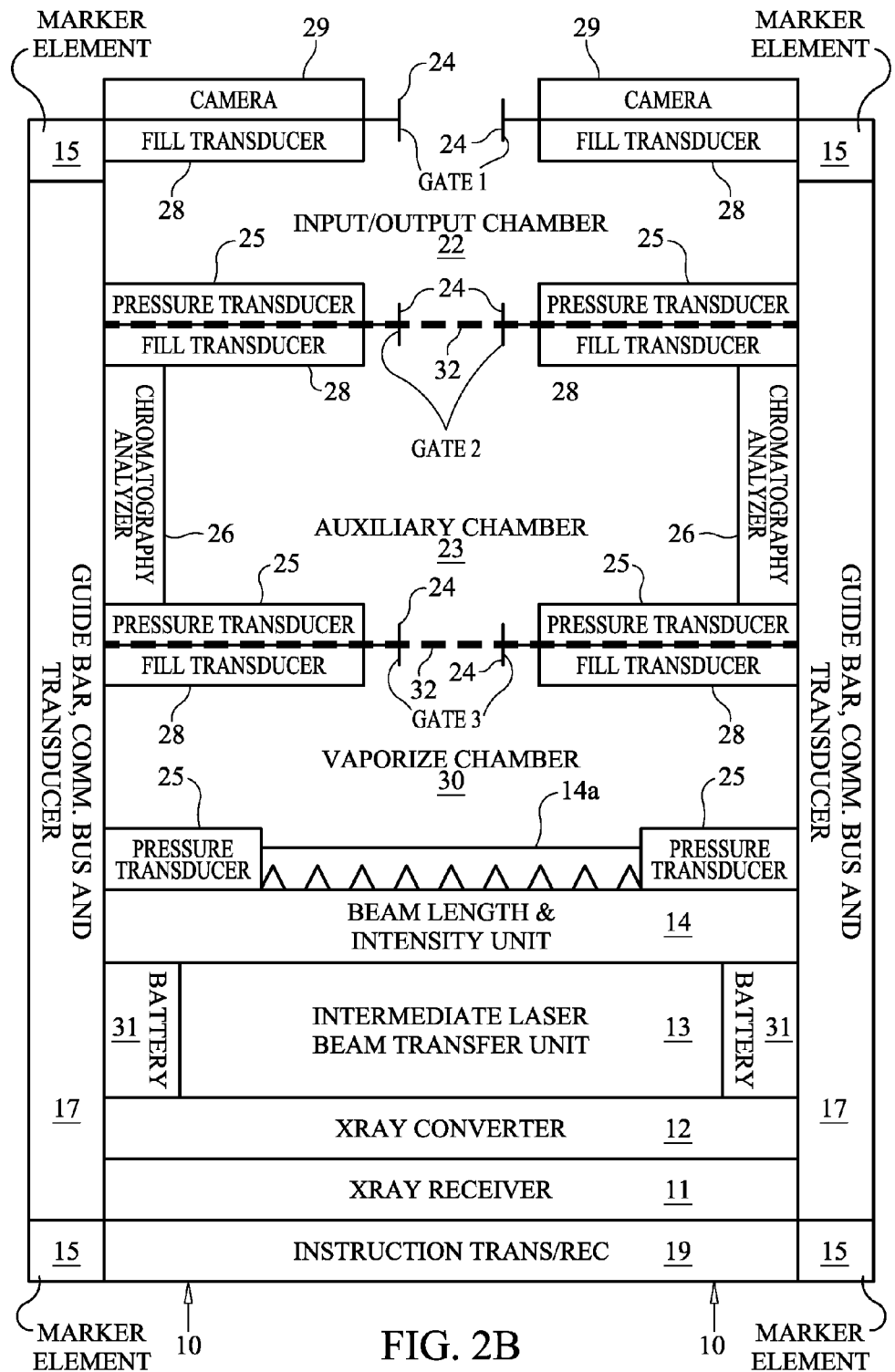
FIG. 2B is a schematic illustration of the module of FIG. 2A, where specified gates are in the closed positions.

FIG. 2A illustrates all of the gates in the open positions. In FIG. 2B, the gates 2-24 and 3-24 are closed, on the auxiliary chamber (23), during the analysis procedure, to trap the material, in the auxiliary chamber. The gates are in the closed positions, as indicated by the phantom lines. After the gates 2-24 and 3-24 to the auxiliary chamber are closed, the fluid, substance or material is analyzed and the results are transmitted to the master machine.

When the module is operating in the vaporizing mode, the pressure transducers (25) will be functioning at all times to continually draw the fluid, substance and the vaporize chamber 30 will constantly vaporize the fluid, substance, material within the chambers.

Figure 3B:
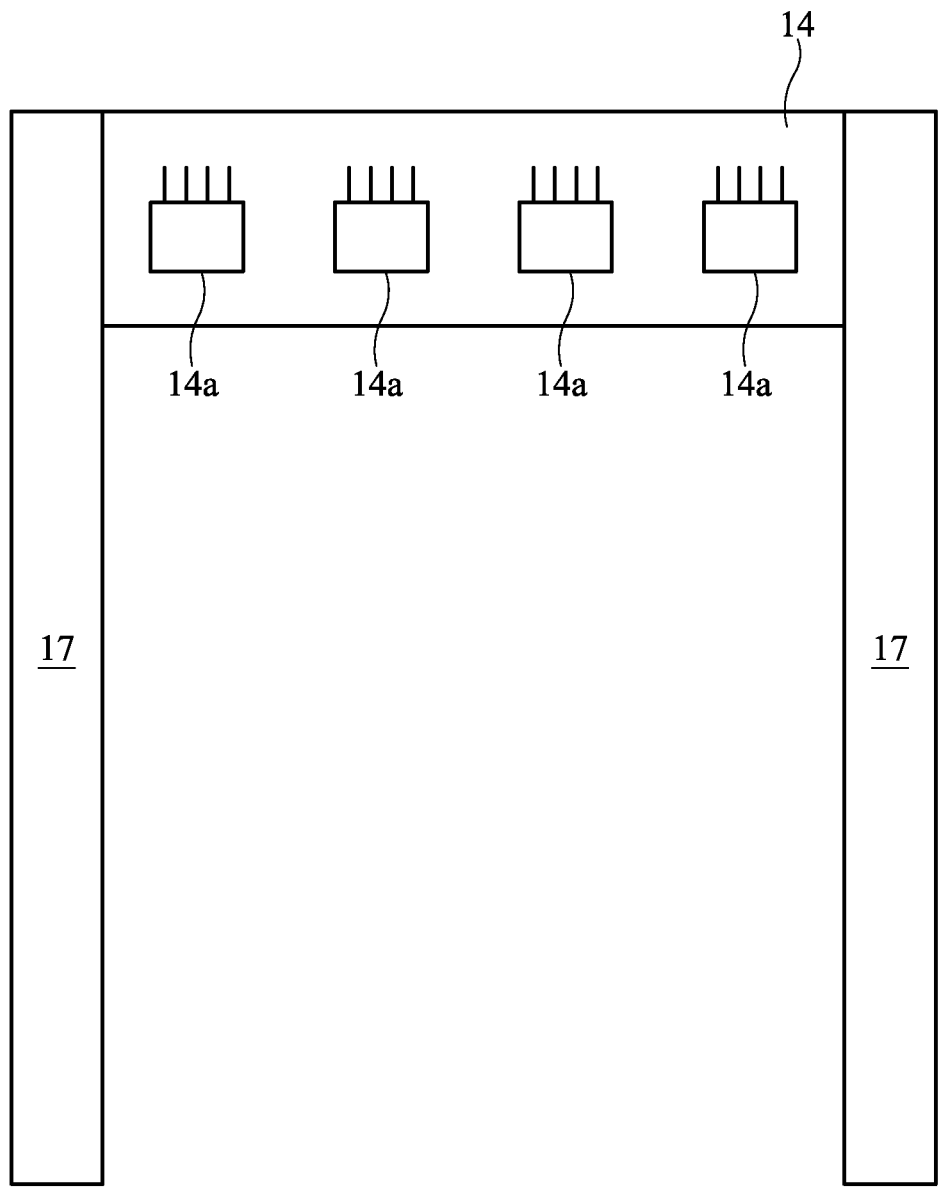
FIG. 3B schematically illustrates a partial view of a biocompatible clearing module having four final beam transmission elements within a final beam transmitter according to an embodiment of the present invention.

FIG. 3B schematically illustrates a partial view of a biocompatible clearing module 10 having four beam transmission elements 14a within a final beam length and intensity unit 14 according to an embodiment of the present invention. The final beam transmission elements 14a include tunable lasers, the outputs of which are controlled by adjustable inputs received via guide bar and communication interface 17 from instructions receiving unit 19.

Figure 4:
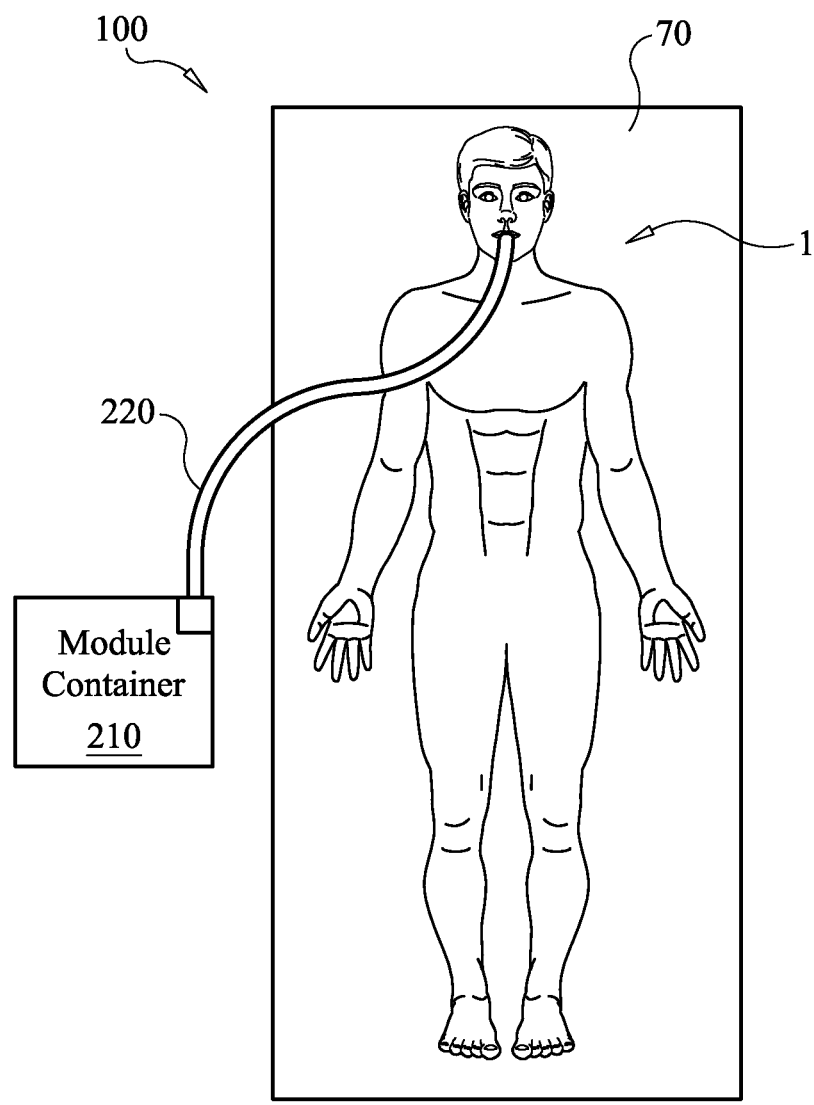
FIG. 4 schematically illustrates a patient inside a main machine of the system during treatment, according to an embodiment of the present invention.

FIG. 4 schematically illustrates a patient 1, inside the main machine of the system 100 during treatment, according to an embodiment of the present invention. A mucus clearing module container 210, accommodates the pre-manufactured clearing modules 10 prepared for use within the system 100. Multiple modules 10 of different sizes may be used, depending upon the requirements of the procedure. Also shown in FIG. 4, is the connection tube 220, to transfer the module 10 from the module container 210 to the patient 1. Transfer of the module 10 from the module container to the patient is accomplished using air transport tube 220. Transfer into the patient's body is initiated by air transport and magnetic force control is used to move the module within the transport connection tube 220 and then within the patient, via the NMR machine 80 of system 100. The same movement control process is used whether module 10 is inserted into a cavity, or other duct or vessel, such as in the urinary duct system, bronchial tubes, glandular ducts, or any other tube or duct in the patient's body, including transoral introduction into the esophagus, as shown in FIG. 4.

Figure 5:
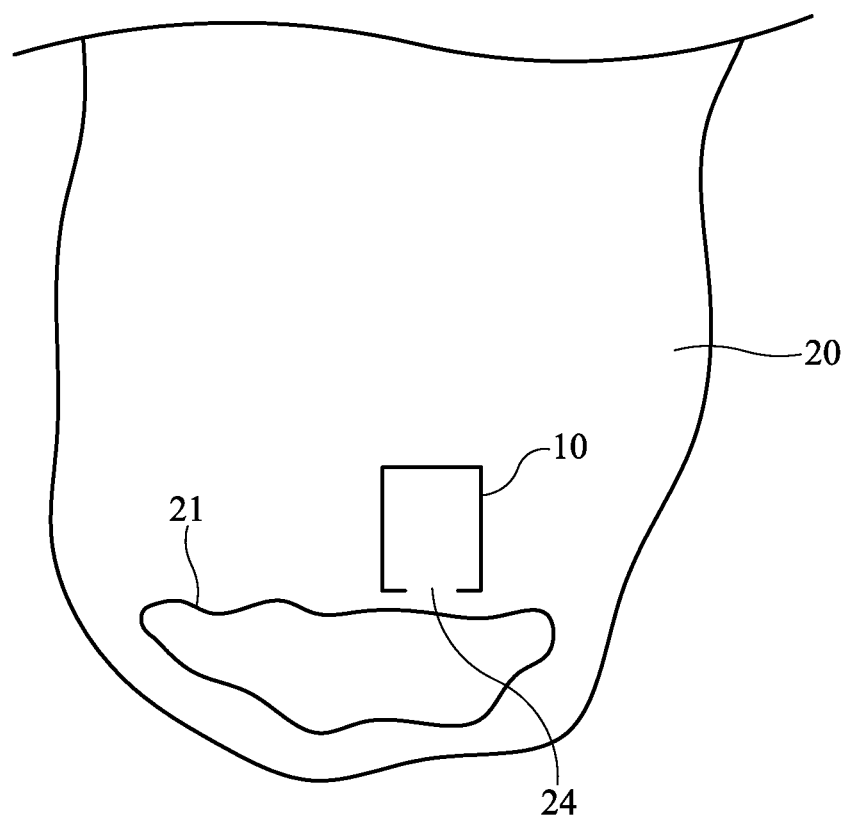
FIG. 5 is an illustration of a lung in need of analysis and/or clearing.

FIG. 5 is an illustration of lower lung cavity area 20 with a fluid, substance or material 21 in need of analysis and/or clearing. The fluid, substance, material 21 (e.g., mucus, fluid, substance, etc) is indicated within the cavity 20. The mucus-clearing module 10, is positioned with the input/output chamber's gate 24 open, as indicated within the cavity. The module 10 is positioned to draw into the module the fluid, substance or material to process.

Figure 6A:
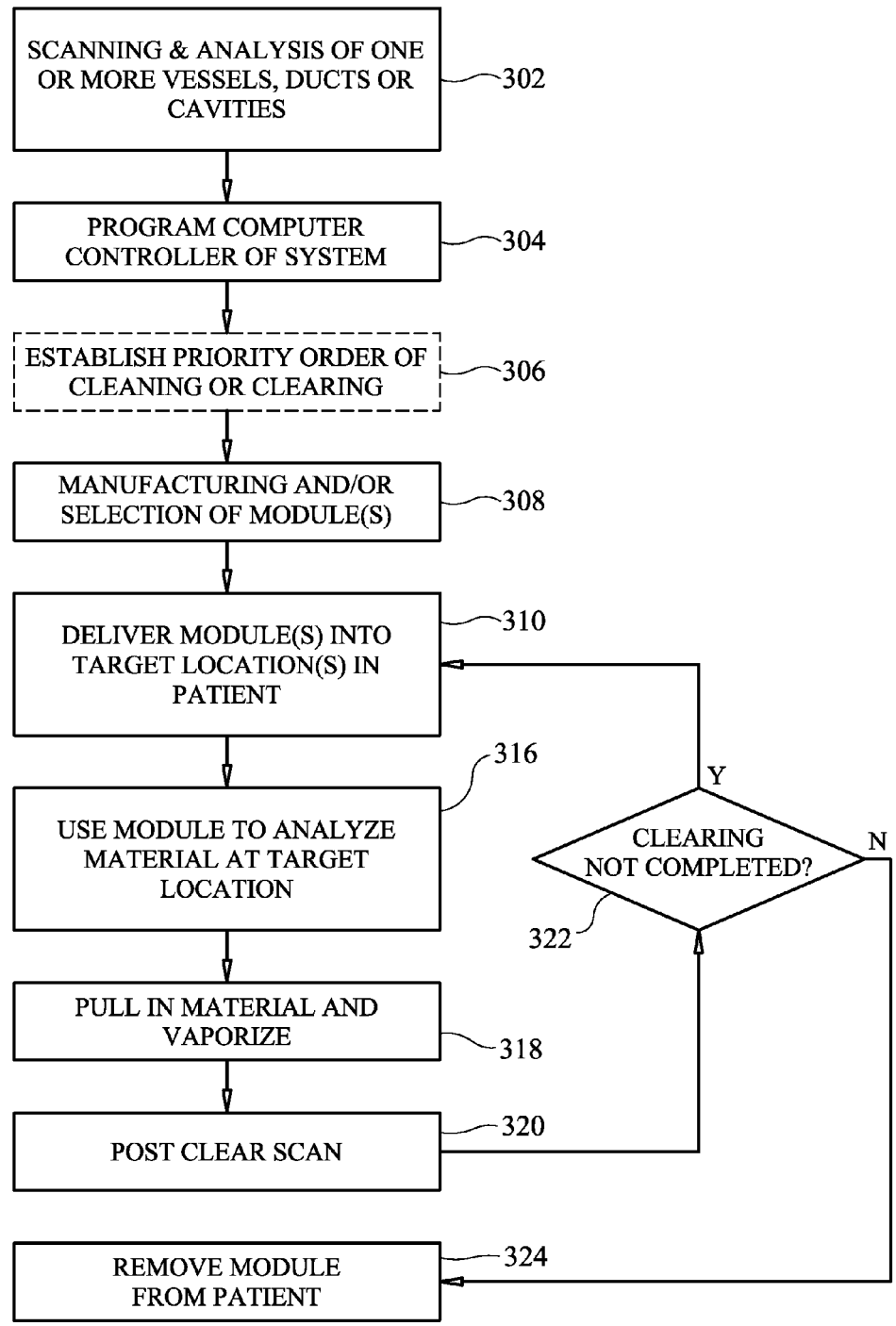
FIG. 6A is a flow chart illustrating events that may occur during a mucus clearing procedure according to an embodiment of the present invention.

FIG. 6A is a flow chart illustrating events that may occur during an analysis and clearing procedure according to an embodiment of the present invention. At event 302, scanning and analysis of a patient 1 are conducted. The patient 1 is scanned using CT or MRI technology. The scan and analysis may be conducted on a single vessel, duct or cavity only or any number of vessels, ducts or cavities up to and including any or all vessels and/or ducts and/or cavities in the patient's body. The results of the scan are analyzed by the administrator of the scanning procedure and/or consulting physicians. This scanning also provides a path for the module to the surgery target area and the substance, fluid, material at the surgery target area.

The procedure with respect to the analysis and/or clearing of the material within vessels, ducts, cavities is performed to determine the location(s) of the material, fluid, etc or target location to be treated and the path to the target location. This analysis 302 can be performed, for example, by performing a CAT scan of the patient 1, using the CAT scan sub-section 90 of system 100. The exact coordinates of the material(s) within the artery(ies) or vein(s) or other vessel(s), duct(s), cavity(ies) in need of treatment are determined, in order to provide a map thereof for reference thereto by NMR sub-section 80 during performance of the delivery and implementation of the module(s) 10.

As a result of the analysis, the location of the material within the vessel/duct/cavity is identified and it is determined that the material should be treated by the clearing module 10. Then the location(s) of the sites to be treated by module (10) and the path(s) are programmed (event 304) into a control computer of system 100, such as at control station 95. The programming provides a map of a target surgical location of a targeted area and the path to the targeted area. The map created by the scanning provides coordinates of landmarks within the physiology of the patient, including coordinates of the vessel, duct or cavity to be targeted and the coordinates of the location of the material(s) that is/are to be the surgical target locations for operation thereon by module 10. The coordinates of the surgical target location(s), vessel(s), duct(s), or cavity(ies) containing the surgical target location(s) and, optionally, any other physiological landmarks that may be useful in navigating the module 10 within the patient 1 are programmed into a computer controller at event 304, of the target surgical location(s) relative to the map.

Optionally event 306 may be carried out to establish a priority of order in which multiple surgical target locations are treated. The establishing of the priority of order may be accomplished by a surgeon, a medical team, or any other entity with the surgical expertise and sufficient knowledge of these surgical techniques qualifying them to do so. An algorithm used by the controlling computer 95 can use the priority list to ascertain a sequence in which the modules 10 are manufactured and arranged in module container 210. Or a range of different sizes of modules 10 may be pre-manufactured, and the algorithm may be used to select the sizes of pre-manufactured modules 10 that are needed for the procedure(s). The modules 10 are manufactured before they are placed into module container 210. The algorithm may further be used to establish the priority regarding the order of deployment of the modules 10 into the vessels, ducts or cavities in need of the procedure. If there is only one module 10 to be manufactured or selected and introduced or if there is no particular criticality in the order in which a multiplicity of modules 10 are assembled and placed within the body, then optional event 306 need not be carried out.

At event 308 the one or more modules 10 to be delivered into the patient 1 are manufactured and/or selected. Typically no more than two or three modules 10 are inserted into one entry location during a procedure, without first removing one or more additional modules 10. Preferably only one module 10 per entry point is inserted. Once all modules 10 needed for the procedure are ready for delivery into the patient 1, the patient 1 is prepared, including inserting tube 220 into a vessel, duct, tubular tissue or body opening through which module(s) 10 can be delivered to the surgical target site(s). There may be more than one tube 220 inserted into more than one vessel, duct or other tubular tissue of the patient 1, depending upon the locations of the surgical target sites, which may determine the starting locations for entry into the patient. The modules 10 are loaded into module container 210 (there may also be multiple module containers 210 when multiple tubes 220 are used to access multiple entry points in the patient 1) in the proper order, if there is one, such as determined at event 306, for example, using any information having been inputted with regard to dimensions of modules 10 needed, as well as priority of movement. Module sizes will vary depending primarily upon the cross-sectional diameter and conformation of the vessel/duct/area that it is to be delivered into, as measured near the surgical target location, but also including conformational features of vessels/ducts that the module 10 needs to pass through to reach the surgical target area. For example, the width of the module 10 needs to be less than the diameter of the vessel/duct/cavity/area adjacent the surgical target location. The length of the module may need to be varied not only according to the diameter of the vessels/ducts/cavities that it is to pass through, but may also be affected by the conformation. For example, the length of a module 10 that needs to traverse a tortuous pathway may need to be shorter than the length of a module 10 that traverses a relatively straight pathway, even though the inside diameter of the vessel adjacent the surgical target area is the same in both cases. For arteries, the module dimensions are typically no greater than about 1.0 cm in length and 0.5 cm in width. Modules may be as small as about 1000 nanometers in length and about 500 nanometers in width, such as for use in capillaries, for example. All sizes within the above two examples are also possible. Modules 10 larger than 1.0 cm in length and 0.5 cm in width can also be manufactured. Each module 10 has a unique identification (ID) code that it can be addressed by, that is unique in that it is different from the identification codes of all other modules 10.

At event 310 the one or more modules 10 are delivered into the patient 1 through one or more vessels, ducts, cavities and/or body openings in which one or more conduits 220 have been inserted; and transported to locations adjacent surgical target locations in the body of the patient, respectively. The system 100 guides and controls the modules 10 based on the locations of the modules 10 and the targeted locations previously established as the surgical target sites. The buffer transducer and guide bars 17 keep the module 10 at safe distances from the cavity walls, vessel walls and/or duct walls. The transducers (e.g., ultrasound transducers or other types of transducers usable for measuring distance, such as by Doppler effect, for example) in the guide, communication bus and transducer bars 17 determine the distance of the module from the cavity walls, vessel walls and duct walls: regularly feedback this distance information to a predetermined algorithm, the road map which has pre-calculated safe distance values all along the route to the surgical target location. This feedback loop is used to control positioning of the module 10 to ensure that it maintains a safe distance from the walls of the vessel at all times. The guiding is performed by registering the movements of the module 10 with the map to provide precise navigation of the module 10 through the anatomy and to the target surgical location.

The operator at the control panel 95 can visually monitor (e.g., on one or more computer monitors 95M) the locations of the modules 10, as well as the surgical target locations, and other related structures and landmarks within the patient (displayed on the map), including, but not limited to the vessel, cavity or duct that the module 10 is travelling through. Thus, the operator can continuously (or intermittently) view the locational relationship of each module 10 and the vessel, cavity or duct it is currently travelling through, as well as its positional relationship relative to the vessel, cavity or duct and surgical target site that it is intended to treat, in real time. The operator can stop or pause the procedure at any time needed via control of the NMR machine 80 and/or control of modules 81, 82 and/or 83.

At event 310, the module will be positioned at the surgical target area if it has been previously determined that a procedure is necessary. This operation may be determined during the scan and analysis phase 302.

At event 316, the module will be positioned at the surgical target area if it has been previously determined that a material or substance must be analyzed by the module to treat a medical condition. The material (substance) is drawn into the modules' auxiliary and analysis chamber 23 by a combination of the negative pressure transducers 25 in each chamber 22/23/30 and the coordinating openings of the gates 24. The negative pressure transducers 25 can draw material into the chambers. The material, fluid or substance will be drawn into the auxiliary & analysis chamber 23 to be analyzed by the chromatography element 26 within the analysis chamber 23. The results of analysis will be transmitted to the master machine.

At event 318, the module will be positioned at the surgical target area to vaporize the material or substance at the surgical target area. Upon reaching a surgical target site and proper positioning of module 10 adjacent to the surgical target site, the material or substance will be drawn into the chambers 22/23/30. The material, fluid will then be vaporized within the vaporize chamber 30. When the module is operating in the vaporizing mode, the pressure transducers will be functioning at all times to continually draw the fluid, substance and the vaporizing function vaporizes the fluid, substance within the chambers. The master machine will send instructions to the module to turn on the vaporizing circuits to vaporize the material or substance. X-ray energy is sent from module 82 to X-ray receiving unit 11, X-ray energy is transferred from unit 11 to X-ray conversion unit 12, X-ray energy is converted to photons by X-ray energy conversion unit 12 and sent to intermediate laser beam transmission unit 13, where the photons are organized into a laser beam and transmitted to multiple final beam transmitters 14a in beam length and intensity unit 14. Elements 14a emit laser energy to the surgical target site to destroy (e.g., vaporize) the material or substance at the surgical target site.

The amount of energy in the laser beam in terms of Watts depends upon the length of the beam, but is on the order of nano Watts. The intensity, length duration, power and all other variable characteristics of the laser beams emitted by elements 14a are algorithmically controlled by the circuits between the electronic interface 122 and the final beam transmitters 14a, as instructed by instructions received from instruction receiving unit 19, and ultimately by controller 95 and instructions transmission module 83 of system 100. The control may be by an algorithmic voltage oscillator where an electrical signal controls the frequency of the oscillator. The frequency of oscillation can be varied by the applied DC voltage, while modulating signals may also be fed into the voltage controlled oscillator to cause frequency modulation (FM) or phase modulation (PM). A voltage controlled oscillator with digital pulse output may similarly have its repetition rate or pulse width modulated. The laser energy is typically applied in bursts. In one embodiment, the module 10 is tracked on the map to an area of the patient's lung (FIG. 5 illustrates a view of beginning an analysis or clearing event, where module 10 is positioned adjacent a surgical target area.

At event 320, a post clearing scan takes place, if the clearing scan indicates that the clearing of the material or substance is not complete, the module 10 will continue drawing in the material or substance until the vaporizing function is completed. At all times, the operator at 95 visually observes the movement and completion of the clearing process. The movement of the module 10 is tracked in relation to the roadmap, guided by a predetermined path to the surgical target area. Also, the operator is aware of the location of the module 10 at all times and if the material/substance has been vaporized.

After executing a clearing event 318 on a surgical target (material or substance to be removed), a scan (e.g., CAT Scan or other visualization) of the target surgical area may be performed 322 to confirm that the module 10 has successfully cleared the material or substance.

At event 320, if it is determined that the material or substance has been satisfactorily cleared, then the module is removed from the patient at event 324. If instead, the material, substance has not been sufficiently or satisfactorily cleared, then processing returns to event 318 where the module repeats application of energy to effect additional clearing. This loop (318-320-322-324) continues until the material or substance has been satisfactorily cleared, at which time, the module 10 can be removed from the patient.

After performance of clearing all material or substance (or otherwise treating all surgical target sites, such as removing other unwanted materials), a post-clear scan may optionally be performed at event 320 to confirm successful completion of the procedures, or to inform the operator if one or more modules 10 need to be used to redo a clearing procedure on one or more surgical target areas. If a particular module 10 is needed for a particular surgical target site, but that module 10 has already been previously removed from the patient 1, the module 10 can be reinserted to perform the procedure again.

Figure 6B:
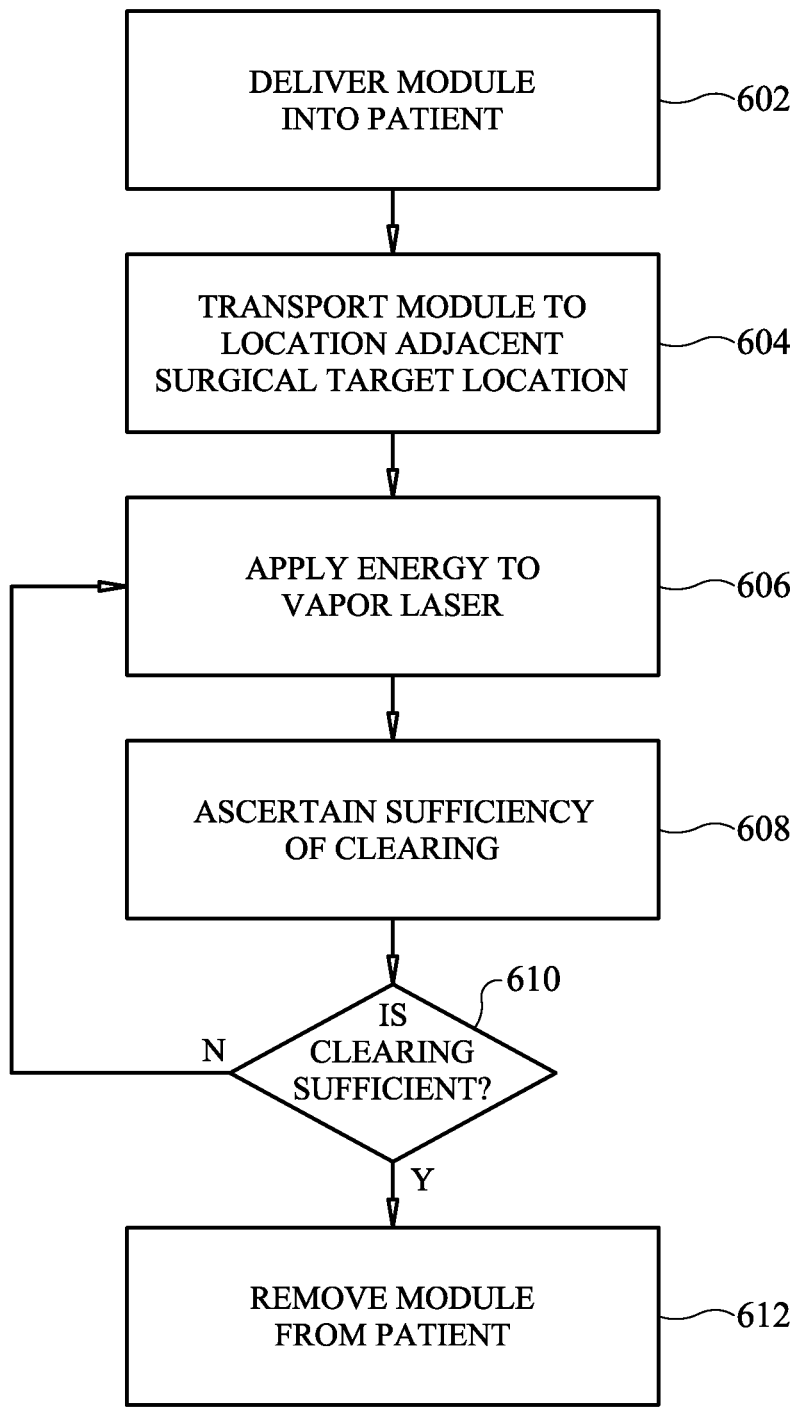
FIG. 6B is a flow chart illustrating events that may occur while performing delivery of one or more devices into a patient, clearing of mucus by vaporizing the mucus.

FIG. 6B is a flow chart illustrating events that may occur while performing delivery of one or more devices to the target area into a patient, and clearing of material or substance from one or more target area/s, and removal of the one or more devices according to an embodiment of the present invention. At event 602 a module 10 is delivered into a vessel, duct or cavity of a patient according to techniques already described herein. At event 604, the module 10 is then transported to a location within a vessel, duct or cavity that is immediately adjacent to a surgical target area. Module 10 is driven and guided via NMR machine 80 (i.e., using magnetic forces applied to module 10) to guide the module 10 along a pathway identified by provision and analysis of the CT or MRI scan described above. The NMR machine utilizes the positioning devices 15 and guide bars 17 to guide the module 10 to the surgical target location. Positioning devices/elements 15 ensure the module 10 is aligned to the surgical target within the vessel, duct or cavity 20, as they are located at four corners of the module 10 and their positions relative to the cavity 20 wall can be monitored by the master machine 100. Positioning elements 15 may be magnetic, or include a radioactive tracing element, and/or be radiopaque and/or have some other characteristic that allows its position to be traced from outside the patient's body. The NMR machine 80 tracks the movement of the module along the programmed roadmap so the module 10 is maintained in a predetermined position, relative to the vessel walls, duct walls or cavity walls, along the route to the surgical target area at all times. Safe distances from the vessel walls are predetermined by the algorithm/roadmap and will vary depending upon the size of the module 10 and the inside diameter and conformation (e.g., straight, or relative degree of curvature and tortuosity) of the vessel, duct or cavity it is travelling through. In one non-limiting example, a safe distance for a module having a width of 100 nanometers, is in the range of about 10 to about 20 nanometers from the vessel or duct wall. As noted, this can vary considerable depending on the inside diameter of the vessel or duct 20, the conformation of the vessel or duct 20, and the width and length of the module 10. In general, safe distances are typically within the range of about ten to about twenty percent of the width of the module 10, although these safe distances may vary. Feedback information is provided by the buffer transducer within guide bars 17 as to the proximity of the bars 17 to the vessel walls, duct walls or cavity walls. This feedback is continuously fed back to the NMR machine 80, and NMR machine 80 uses the feedback to maintain the module 10 at a safe distance from the vessel, duct or cavity walls at all times. The buffer transducer(s) may be in the form of an ultrasound emitter and receiver, for example.

Once it has been confirmed (by the operator of the control station 95 visually observing, on monitor 95M, the module 10 adjacent the surgical target location) that the module 10 has been accurately placed in a position immediately adjacent the surgical target location and oriented to remove the material or substance as required, the algorithm turns on the circuitry to draw in the material, substance and apply energy to the vaporizing lasers. The position and orientation of the module 10 are then accurately maintained using magnetic forces applied by NMR machine 80, as controlled by continuous feedback provided by positioning elements/devices 15 and bars 17 and destructive energy is applied to the material within the vaporizing chamber 30 to vaporize the fluid, material or substance at the surgical target location.

After completing a session of application of energy at event 606, or alternately during performance of event 606 (monitoring either continuously or intermittently), monitoring is performed at event 608 to ascertain whether and when the material, substance has been sufficiently cleared from the vessel/duct/cavity. Monitoring can be performed visually on monitor 95M by the operator of the control station 95 and/or via direct feedback from the module 10, such as may be provided by visualization features such as ultrasonic imaging or other form of onboard imaging. If it is determined at event 610 that the obstruction/blockage has not been sufficiently cleared, then processing returns to event 606 where energy is again applied to the surgical target by the module 10. Loop 610-606-608-610 continues until the material, substance has been sufficiently cleared. Once the material, substance has been determined to be sufficiently cleared at event 610, then the module 10 is removed from the patient at event 612.

Figure 7:
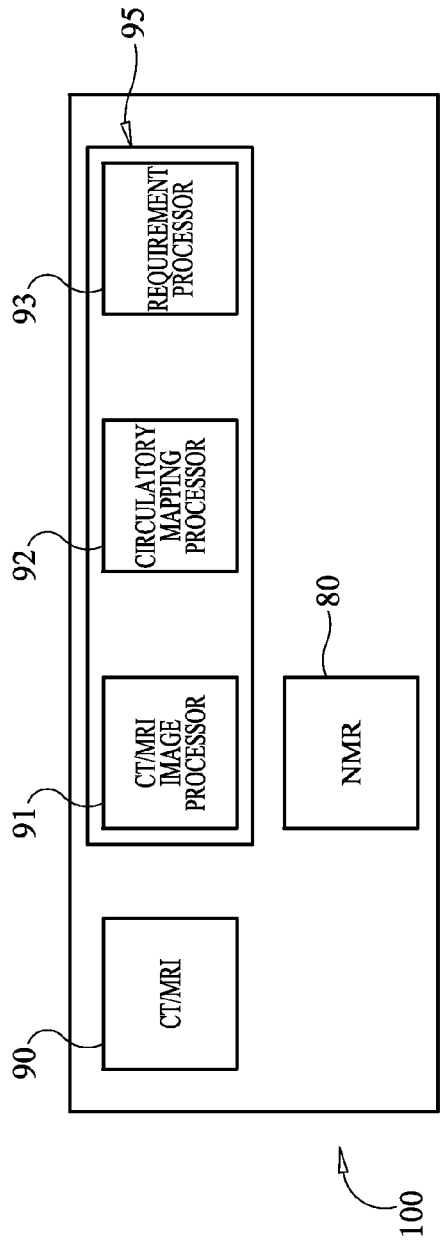
FIG. 7 is a schematic illustration of hardware components included in a system according to an embodiment of the present invention.

FIG. 7 is a schematic illustration of hardware components included in system 100 according to an embodiment of the present invention. Data sent from the CT/MRI section 90 from the clamshell after mapping is sent to the CT/MRI image processor section 91, the circulatory mapping processor 92 and the requirement processor 93 for analysis and programming of the roadmap, requirements and instructions to be executed with the computer 95. The CT/MRI subsystem 90 obtains data for mapping the vessel system to be traversed as well as surgical target location(s). This data is mapped so that coordinates can be relied upon by the NMR subsystem 80 to drive and position the module 10 within the patient 1. The data obtained by the CT/MRI subsystem 90 is processed by the CT/MRI image processor 91 and the image-processed data is transferred to the circulatory mapping processor 92. Processor 92 further processes the image-processed data to output a detailed map of the vessel system to be traversed and surgical target location(s) all mapped to coordinates relative to the patient 1. The requirement processor then generates an algorithm and provides it for use by the NMR subsystem 80 to reference for guiding and positioning module 10.

Figure 8:
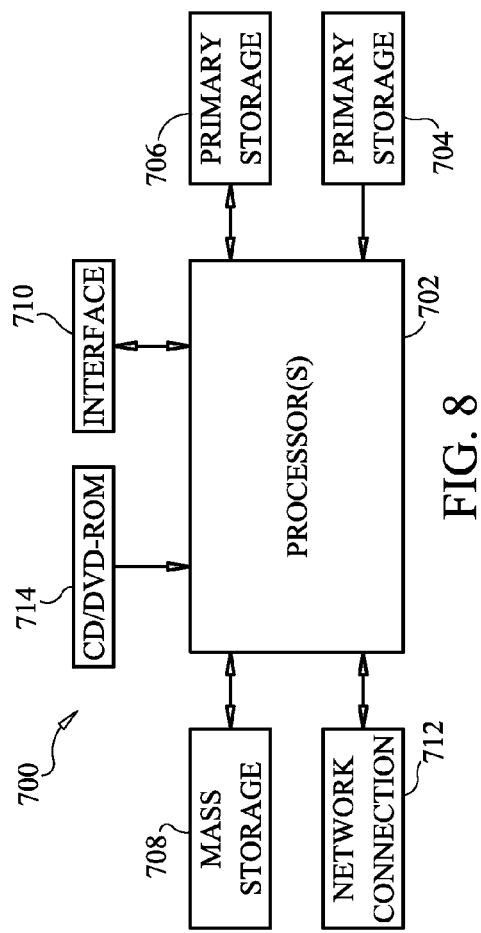
FIG. 8 is a block diagram of a computer system that may be implemented in a system according to an embodiment of the present invention.

FIG. 8 is a block diagram of a computer system that may be implemented in system 100 according to an embodiment of the present invention. This figure represents a typical computer system, components of which, or all of which may be employed in system 100. The computer system 700 includes any number of processors 702 (also referred to as central processing units, or CPUs, and, for example, which may be employed in the computer controller 95 of system 100, as well as one or more sub-sections described) that are coupled to storage devices including primary storage 706 (typically a random access memory, or RAM), primary storage 704 (typically a read only memory, or ROM). As is well known in the art, primary storage 704 acts to transfer data and instructions uni-directionally to the CPU and primary storage 706 is used typically to transfer data and instructions in a bi-directional manner. Both of these primary storage devices may include any suitable computer-readable media such as those described above. A mass storage device 708 is also coupled bi-directionally to CPU 702 and provides additional data storage capacity and may include any of the computer-readable media described above. Mass storage device 708 may be used to store programs, data and the like and is typically a secondary storage medium such as a hard disk that is slower than primary storage. It will be appreciated that the information retained within the mass storage device 708, may, in appropriate cases, be incorporated in standard fashion as part of primary storage 706 as virtual memory. A specific mass storage device such as a CD-ROM or DVD-ROM 714 may also pass data uni-directionally to the CPU.

CPU 702 is also coupled to an interface 710 that includes one or more input/output devices such as video monitors, track balls, mice, keyboards, microphones, touch-sensitive displays, transducer card readers, magnetic or paper tape readers, tablets, styluses, voice or handwriting recognizers, or other well-known input devices such as, of course, other computers, any of which may be included in console 95, for example. Interface 710 may include interfaces to NMR 80 and CT/MRI 90 sections, and the like. Finally, CPU 702 optionally may be coupled to a computer or telecommunications network using a network connection as shown generally at 712. With such a network connection, it is contemplated that the CPU might receive information from the network, or might output information to the network in the course of performing the above-described method steps. The above-described devices and materials will be familiar to those of skill in the computer hardware and software arts.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A module for insertion into a living body, said module comprising:
    an instructions receiver configured to receive wireless transmissions of instructions from an apparatus located outside of the body when said module is inside the body;
    an opening in a surface of said module, said opening communicating with a first chamber within said module, said opening and said first chamber being configured and dimensioned to receive material from inside the body when said module is inserted into the body;
    a first gate configured to open and close said opening in the surface of the module;
    a second chamber configured to receive the material from the first chamber and containing an analyzer;
    a second gate configured to open and close a second opening between said first and second chambers;
    a third chamber configured to receive the material from the second chamber;
    a third gate configured to open and close a third opening between said second and third chambers
    wherein said analyzer is configured to analyze composition of the material received in said second chamber;
    an energy emitter configured to vaporize the material received in the third chamber; and
    a transmitter configured to wirelessly transmit composition analysis results produced by said analyzer to said apparatus.

2. The module of claim 1, further comprising a negative pressure generator configured to generate negative pressure in each of said first, second and third chambers to draw the material in the body into said respective chambers.

3. The module of claim 1, further comprising a camera configured to capture images of the body when said module is inserted in the body, wherein said module wirelessly transmits said images to said apparatus outside the body.

4. The module of claim 1, wherein said analyzer comprises a liquid chromatography analyzer.

5. The module of claim 1, further comprising a negative pressure generator configured to generate negative pressure in said first chamber to draw the material into said first chamber.

6. The module of claim 1, wherein said module is configured to be moved and guided wirelessly within the body by said apparatus located outside of the body.

7. The module of claim 6, wherein said module is configured to be moved and guided by nuclear magnetic resonance.

* * * * *